United States Patent [19]
Houghten

[11] Patent Number: 4,545,931
[45] Date of Patent: Oct. 8, 1985

[54] **SYNTHETIC HEAT-STABLE ENTEROTOXIN POLYPEPTIDE OF *ESCHERICHIA COLI***

[75] Inventor: Richard A. Houghten, Solana Beach, Calif.

[73] Assignee: Scripps Clinic and Research Foundation, La Jolla, Calif.

[21] Appl. No.: 455,265

[22] Filed: Jan. 3, 1983

[51] Int. Cl.$^4$ ............................................ C07C 103/52
[52] U.S. Cl. ............................................ 260/112.5 R
[58] Field of Search ............................... 260/112.5 R

[56] References Cited

PUBLICATIONS

Infect. Immun. 37, 550–557, (1982).
Proc. Nat'l. Acad. Sci. 77, 4011–4015, (1980).
J. Biol. Chem., vol. 256, (1981), 7744–7746.

*Primary Examiner*—Delbert R. Phillips
*Attorney, Agent, or Firm*—Dressler, Goldsmith, Shore, Sutker & Milnamow, Ltd.

[57] ABSTRACT

A synthetic polypeptide having at least about 40% of the antigenicity of biologic heat stable enterotoxin of *E. coli*. The synthetic polypeptide includes at least 14 amino acids in the sequence, from amino-terminus to carboxy-terminus, represented by the formula: CysCys-GluLeuCysCysTyr(Asn)ProAlaCysAla(Thr)-GlyCysAsn(Tyr) wherein the amino acid in parentheses may replace the immediately preceding amino acid residue, and at least one intramolecular disulfide bond formed between the Cys residues. The Cys residues that are not part of the intramolecular disulfide bond can be replaced by other amino acid residues or be bonded to substituent moieties.

12 Claims, 16 Drawing Figures

SYNTHETIC HEAT-STABLE ENTEROTOXIN POLYPEPTIDE OF *ESCHERICHIA COLI*

DESCRIPTION

1. Technical Field

The present invention relates to a synthetic polypeptide corresponding to heat-stable enterotoxin of *Escherichia coli*, and more particularly to synthetic polypeptides that comprise principal determinant domains responsible for the immunogenicity of the *E. coli* heat-stable enterotoxin.

2. Background Art

Acute diarrheal disease due to transient colonization of the small bowel by enterotoxigenic strains of *Escherichia coli* (*E.coli* or ETEC) is a major health problem of global scope for both humans and for animal husbandry. These organisms, together with rotavirus, are the principal cause of the often fatal acute diarrhea that is common among infants living in underdeveloped countries and among neonatal animals, particularly lambs and piglets. ETEC strains are also the usual cause of acute diarrhea among persons from temperate zones who travel to the tropics, and may be responsible for sporadic or epidemic episodes of diarrhea among children and adults living in either temperate or tropical areas.

The disease caused by ETEC is mediated by the release of two enterotoxins, either singly or together. The large molecular weight, antigenic heat-labile toxin (LT) has been purified to homogeneity and its subunit structure characterized as five B subunits which attach the holotoxin to the specific $GM_1$ ganglioside receptors on the mucosal surface, and a single A subunit which stimulates intracellular adenylate cyclase activity, thus evoking fluid and electrolyte secretion.

The low molecular weight, heat-stable toxin (ST) produced by ETEC strains of human or porcine origin has also recently been purified. Preparations of ST have a relatively high content of half-cystine, cause secretion by stimulating guanylate cyclase and are haptenic as evidenced by their capacity to raise an antitoxin response in animals immunized with the toxin coupled to a large molecular weight carrier.

The most practical approach for the prevention of ETEC-induced diarrhea would be an immunization program that provides protection against heterlogous ETEC serotypes that produce either or both of the LT or ST enterotoxins. Immunization with either the biologic LT or the biologic ST toxin evokes an antitoxin response in experimental animals that protects against homologous and heterologous serotypes of strains that produce the specific toxin used for immunization. Immunization with the LT whole toxin or its B subunit yields protection against viable heterlogous strains that produce this toxin alone (LT+/LT−) or together with ST (LT−/ST−), but not against those which make just ST (LT−/ST+).

Immunization with biologic ST coupled to a large molecular weight carrier arouses serum antibodies that passively neutralize the secretory effect in the suckling mouse model of ST produced by heterlogous strains. Immunization also provides protection against direct challenge with viable heterlogous LT−/ST+, but not LT-producing strains. Neither of these toxins are suitable for immunization when given alone, however, in view of their toxicity, their failure to provide protection against strains which produce the other toxin form, and the fact that the large molecular weight carriers that have been used to render the haptenic biologic ST molecule immunogenic are unsuitable for human use.

Klipstein et al., *Infect. Immun.*, 37:550-557 (1982) have reported the development of a vaccine made by conjugating the biologic ST toxin to the LT toxin by means of the carbodiimide reaction. As a result of that reaction, biologic ST acquires immunogenicity when coupled to the large molecular weight LT carrier, while both cross-linked toxins retain most of their antigenicity but loose most of their toxic properties. Rats immunized with the vaccine so produced were strongly protected against challenge with either LT or biologic ST and with viable ETEC strains which produce those toxins.

A semi-pure preparation of biologic ST was used for that vaccine because of the relatively low yield of pure biologic ST obtained by the available purification techniques which involve multiple chromatographic separation steps. The inclusion of the heterogeneous material in the vaccine may preclude its use for human immunization, however.

The present invention, relating to the synthetically produced ST, has overcome the problem of using ST derived from natural sources in that synthetic ST can be made in large quantities and in purified form, and has properties similar to those described for pure ST obtained by bacterial growth of a human ETEC strain. [Staples et al., *J. Biol. Chem.*, 255:4716-4721 (1980); and Chan et al., *Ibid.*, 256:7744-7746 (1981)].

At least two types of ST have been identified by their physical properties. The first type known as ST I (also referred to as STa) is soluble in methanol and is active in the suckling mouse model. The second type, ST II (also referred to as STb) is methanol insoluble and not active in the suckling mouse model, but is active in ligated pig ileal loops.

Among the ST I polypeptides, at least three similar polypeptides, or determinant domains of those polypeptides, have been identified, and their amino acid sequences determined. These three types of ST I are referred herein as (i) ST Ia which was initially found in a bovine *E. Coli* strain and a portion of which is also encoded in porcine strains, (ii) that designated ST Ib from a human isolate of *E. Coli* and (iii) ST Ic also isolated from human-infecting *E. coli*.

The nucleotide sequence coding for the ST Ia polypeptide has been determined. Translation of the nucleotide sequence into a polypeptide amino acid sequence leads to a polypeptide that contains 72 amino acids capped at the carboxy-terminus with a tyrosine group [So et al., *Proc. Natl. Acad. Sci. USA*, 77:4011-4015 (1980)]. The ST Ic polypeptide is thought to also contain 72 amino acids as well as several homologous domains with the ST Ia polypeptide. The ST Ib polypeptide is reported to contain only 18 amino acids [Chan et al., *J. Biol. Chem.*, 256:7744-7746 (1981)].

The 18 amino acids of the ST Ib polypeptide show great homology to amino acids 55 through 72 for the polypeptide of ST Ia. The homologous, almost identical, region is illustrated hereinbelow, beginning on the left at amino acid number 55 from the amino-terminus of the ST Ia polypeptide:

ST Ia: AsnThrPheTryCysCysGluLeuCysCys

ST Ib: AsnThrPheTyrCysCysGluLeuCysCys

AsnProAlaCysAlaGlyCysTyr
TyrProAlaCysAlaGlyCysAsn

Examination of the above 18-amino acid polypeptide sequences reveals that six half-cystine (Cys) residues that are present. Oxidation of those half-cystine residues to cystine residues containing intramolecular disulfide bonds in the naturally occuring enterotoxin is thought to lend the observed heat stability to that material.

It is further noted, however, that while cystine disulfide bonds are known to be present in biologic ST, it is not known which pairs of half-cystine residues combine to form the three disulfide bonds which are present in the native ST molecule. Those three disulfide bonds can theoretically be formed from fifteen different combinations of the six Cys residues present.

Staples et al., supra., have shown that the disulfide linkages of biologic ST are required for biological activity of the toxin. Thus, chemical reduction to form half-cystines or performic acid oxidation to cysteic acid was shown to destroy the biological activity of the toxin. In addition, Chan et al., supra., have reported that the first four residues from the amino-terminus of the homologous 18-amino acids of the above sequence of ST Ib are not required for biological activity. Thus, biological activity was obtained from the amino acid-containing polypeptide comprising the above carboxy-terminal 14 amino acids and their disulfide bonds.

SUMMARY OF THE INVENTION

The present invention relates to a synthetic polypeptide having an antigenicity that is at least about 10 percent of that of biologic *E. coli* heat-stable enterotoxin (ST). The synthetic polypeptide includes the amino acid residue sequence, taken left to right and in the direction from amino-terminus to carboxy-terminus, represented by the formula:

$$\underset{|}{R_a^1} \quad \underset{|}{R_b^2} \quad \quad \underset{|}{R_d^4}$$
$$Cys(R_g^7)Cys(R_h^8)GluLeuCys(R_i^9)Cys(R_j^{10})Tyr(Asn)$$
$$\underset{|}{R_c^3}$$

$$\underset{|}{R_e^5} \quad \quad \underset{|}{R_f^6}$$
$$ProAlaCys(R_k^{11})Ala(Thr)GlyCys(R_l^{12})Asn(Tyr)$$

wherein the three specific amino acid residues in parentheses are each an alternative to the immediately preceding amino acid residue in the sequence;

a–f and g–l are integers each having a value of zero or one, whereby if the value of any of a–f or g–l is zero, the corresponding $R_{a-f}^{1-6}$- or $R_{g-l}^{7-12}$-group is absent, while if the value of the a–f or g–l is one, the corresponding $R_{a-f}^{1-6}$-or or $R_{g-l}^{7-12}$-group is present;

the $R_{a-f}^{1-6}$-groups, when taken individually, are the same or different moieties bonded to the sulfur atom of the Cys residue and are selected from the group consisting of hydrogen, an alkyl group containing 1 to about 4 carbon atoms, and a substituted alkyl group containing 2 to about 20 carbon atoms;

the $R_{g-l}^{7-12}$-groups are the same or different alternative amino acid residues to each immediately preceding Cys residue; and at least two of a–f and two of g–l are zero and two Cys residues are present whereby the synthetic polypeptide contains at least one intramolecular disulfide bond formed between the at least two Cys residues present.

In more preferred practice, with reference to the above formula for the immunogenic synthetic polypeptide:

a–f are integers having a value of zero or one with the proviso that:
"e" is zero when "a" is zero,
"d" is zero when "b" is zero, and
"f" is zero when "c" is zero;

the further proviso that at least one of "a", "b" or "c" must be zero whereby the corresponding $R_{a-c}^{1-3}$ is absent as is the $R_{d-f}^{4-6}$ whose subscript is zero when said "a", "b" or "c" is zero and an intramolecular disulfide bond is present between the respective Cys residues for which a subscript value of zero requires another subscript value to be zero; and when a value of a–f is one, said $R_{a-f}^{1-6}$-groups, when taken individually, are the same or different moieties bonded to the sulfur atom of the Cys residue and are selected from the group consisting hydrogen, an alkyl group containing 1 to about 4 carbon atoms and a substituted alkyl group containing 2 to about 20 carbon atoms;

wherein g–l are integers having the value of zero or one, as noted above, with the proviso that:
each of "g" and "k" is zero when "a" is zero,
each of "h" and "j" is zero when "b" is zero, and
each of "i" and "l" is zero when "c" is zero; and when the value of g–l is one, the $R_{g-l}^{7-12}$-groups are the same or different alternative amino acid residues to each immediately preceding Cys residue.

The immunogenic synthetic polypeptide can thus be seen to contain at least one intramolecular disulfide bond of a cystine residue formed between two Cys residues. In the more preferred embodiments, that cystine disulfide bond is formed between the pairs of Cys residues of groups $R_a^1$ and $R_e^5$, $R_b^2$ and $R_d^4$, or $R_c^3$ and $R_f^6$. In still more preferred embodiments, the synthetic polypeptide contains at least two cystine residues and their disulfide bonds formed between the above pairs of Cys residues, and in most preferred embodiments, the synthetic polypeptide contains three cystine residues between the aforementioned Cys residues.

Biologic ST contains three disulfide bonds formed among the six Cys residues. The most preferred synthetic ST of this invention has an identical 18-amino acid residue sequence to a biologic ST that also contains three intramolecular disulfide bonds formed among its six Cys residues. However, the thin layer chromatographic and electrophoretic mobilities and immunologic properties of biologic and synthetic ST molecules are different even though the two molecules have the same primary structure and each contains three intramolecular disulfide bonds.

The synthetic polypeptide of this invention having at least 10% of the antigenicity of biologic ST may be prepared by synthesizing under non-oxidizing conditions a first, unoxidized polypeptide including the amino acid residue sequence taken from left to right and in the direction from amino-terminus to carboxy-terminus represented by the formula:

$$Cys(R_g^7)Cys(R_h^8)GluLeuCys(R_i^9)Cys(R_j^{10})Tyr(Asn)$$
$$ProAlaCys(R_k^{11})Ala(Thr)GlyCys(R_l^{12})Asn(Tyr)$$

wherein the above amino acid residue sequence without the three specific parenthesized amino acid residues and the $R_{g-l}^{7-12}$-groups correspond to the amino acid residues of the ST Ib polypeptide numbered 5 through 18 from the amino-terminus of that ST Ib polypeptide;

the three specific amino acid residues in parentheses are each an alternative to the immediately preceeding amino acid residue:

$R_g{}^7$, $R_h{}^8$, $R_i{}^9$, $R_j{}^{10}$, $R_k{}^{11}$ and $R_l{}^{12}$ are the same or different alternative amino acid residues to the preceding Cys residue. g-1 are integers having the value of zero or one whereby if any of g-l has a value of zero the corresponding, individual $R_{g\text{-}l}{}^{7-12}$-group is absent, and the value of at least two of $_{g\text{-}l}$ is zero, with the proviso that at least one pair of non-contiguous Cys residues from the Cys residues preceding the individual $R_{g\text{-}l}{}^{7-12}$-groups is present, said non-contiguous pairs of the Cys residues corresponding to amino acid residue positions in the ST Ib polypeptide numbered 5 or 6 and 9 or 10, 5 or 6 and 14, and 9 or 10 and 17 from the amino-terminus of said ST Ib polypeptide. The first, unoxidized polypeptide so prepared is then dissolved in aqueous solution at a concentration of less than about 2 milligrams per milliliter and at a pH value of about 7.5 to about 10.5.

The obtained first polypeptide-containing solution is thereafter contacted with molecular oxygen as an oxidizing agent. The contact between the solution and molecular oxygen is maintained for a period of about 1 to about 24 hours to form at least one intramolecular disulfide bond between at least two of the Cys residues present.

In preferred practice, the disulfide bond is formed between the pairs of Cys residues corresponding to the amino acid residues positions in the ST Ib polypeptide numbered 5 and 14, 6 and 10, and 9 and 17 from the amino-terminus of the ST Ib polypeptide. In more preferred practice, the contact between molecular oxygen and the solution containing the first polypeptide is maintained for a period sufficient to form two disulfide bonds between the above mentioned pairs of Cys residues, and still more preferably to form three, intramolecular cystine disulfide bonds between those pairs of Cys residues.

The present invention has several benefits and advantages. One such benefit is that it provides a source of immunologically active ST which may be prepared in large quantities and in substantially pure form. One of the advantages of the present invention is that the synthetic ST may be used to vaccinate humans and other animals against strains of *E. coli* which produce ST. Another benefit of the present invention is that the synthetic ST may be utilized in a diagnostic reagent or reagent system for assaying the presence of an infection caused by ST-producing *E. coli*. Still further benefits and advantages of the present invention will be apparent to those skilled in the art from the detailed description examples and claims which follow.

BRIEF DESCRIPTION OF THE DRAWINGS

In the drawings forming the portion of this disclosure:

FIG. 1 illustrates the potency of synthetic and biologic ST in inducing fluid secretion in the suckling mouse assay. One mouse unit (MU) is defined as that amount of toxin which yields an intestinal (gut) weight:carcass weight ratio of at least 0.083. Values for MU shown are per microgram of toxin.

FIG. 2 illustrates fluid secretion following instillation of the toxins for 18 hours into ligated ileal loops of fasting rats. Values are microliters of fluid per centimeter of intestinal length. The $ED_{50}$ signifies that dosage in nanograms which evokes one-half of the maximum secretory response.

FIG. 3 illustrates the antigenicity of synthetic and biologic ST determined by a double sandwich technique ELISA using hyperimmune antisera to biologic ST. The antigenicity of the two ST toxins was substantially the same when tested against hyperimmune antisera to synthetic ST.

FIG. 4 illustrates the neutralizing effect of hyperimmune antisera to either synthetic or biologic ST on the secretory effect of toxins in the suckling mouse assay.

FIG. 5 shows the composition and properties of conjugates derived from conjugating an initial molar ratio of synthetic ST to the LT holotoxin of 100:1 in the presence of varying concentrations of the carbodiimide reagent 1-ethyl-3-(3-dimethylaminopropyl) carbodiimide (EDAC). Values for the percent of ST in the final conjugates are based on weight of Lowry protein.

FIG. 6 illustrates the effect of the initial molar ratio of synthetic ST to B subunit on the amount of ST incorporated into the final conjugate as determined using a tracer dose of radio-iodinated ST. The EDAC to conjugate ratio was 2:1.

FIG. 7 illustrates the effect of varying the EDAC to conjugate ratio on the composition and antigenicity of conjugates obtained from an initial molar ratio of synthetic ST to B subunit of 50:1. Antigen units, expressed per 100 micrograms of conjugate, were derived by multiplying the percentage of toxin present (by weight) times the percentage of antigenicity. Circled numbers indicate the ratio of EDAC to each specific toxin.

FIG. 8 illustrates the effect on composition and antigenicity of the conjugates of varying the initial molar ratio of synthetic ST to B subunit. Circled numbers indicate the ratio of EDAC to each specific toxin. The EDAC to conjugate ratio was 1.5:1.

FIG. 9 illustrates protection attained in rats immunized with graded antigen unit dosages of either the B subunit or synthetic ST coupled to porcine immunoglobulin G (PIG). Rats given varying dosages for intraparenteral (i.p.) primary immunization (left) all received a total peroral (p.o.) booster dosage of 2,000 antigen units; those given variable p.o. boosters (right) all received i.p. primary immunization with 200 antigen units. Mucosal IgA antitoxin (mucosal AT) values are the increase in the reciprocal of the geometric mean titer in immunized rats over that of unimmunized controls, squares designate the ST while circles designate the B subunit.

FIG. 10 illustrates protection attained against challenge with the human LT+/ST+ *E. coli* strain compared to that against human LT- or ST- only *E. coli* strains in rats immunized with graded p.o. antigen unit dosages of either the B subunit or synthetic ST coupled to PIG. All rats received i.p. primary immunization with 200 antigen units.

FIG. 11 illustrates the effect of varying the initial molar ratio of ST to the B subunit on the antigenicity of the component toxins in the cross-linked vaccine. The ratio of carbodiimide to conjugate protein was consistently 1.5:1 by weight.

FIG. 12 illustrates the immunogenicity of ST when given coupled to PIG or as a component of the cross-linked vaccine. All rats received (i.p.) primary immunization with 200 ST antigen units and were challenged with the human LT+/ST+ *E. coli* strain. Mucosal AT values are as in FIG. 9.

FIG. 13 illustrates the toxicity of the vaccine in the suckling mouse assay. Values are the mean ± standard error of the mean for 3 mice for each datum point. MED, minimum effective dosage, is that dosage that yields a positive response of a gut:carcass weight ratio of at least 0.083.

FIG. 14 illustrates the toxicity of the vaccine in rat ligated ileal loops. Values are the mean ± standard error of the mean for 3 rats for each datum point. $ED_{50}$ is that dosage which yields one-half of the maximum secretory response. "Heated" indicates the vaccine was exposed to 65° C. for 1 hour prior to testing.

FIG. 15 illustrates protection attained in immunized rats. The horizontal line designates 50% of maximum secretion in unimmunized animals, and $ED_{50}$ signifies that dosage which produced this value in this group of rats. PI signifies protection index and i.p./p.o., the immunization route.

FIG. 16 illustrates protection attained in immunized rabbits. Designations are the same as in FIG. 15.

DETAILED DESCRIPTION OF THE INVENTION

I. Synthetic ST

Figure 4:
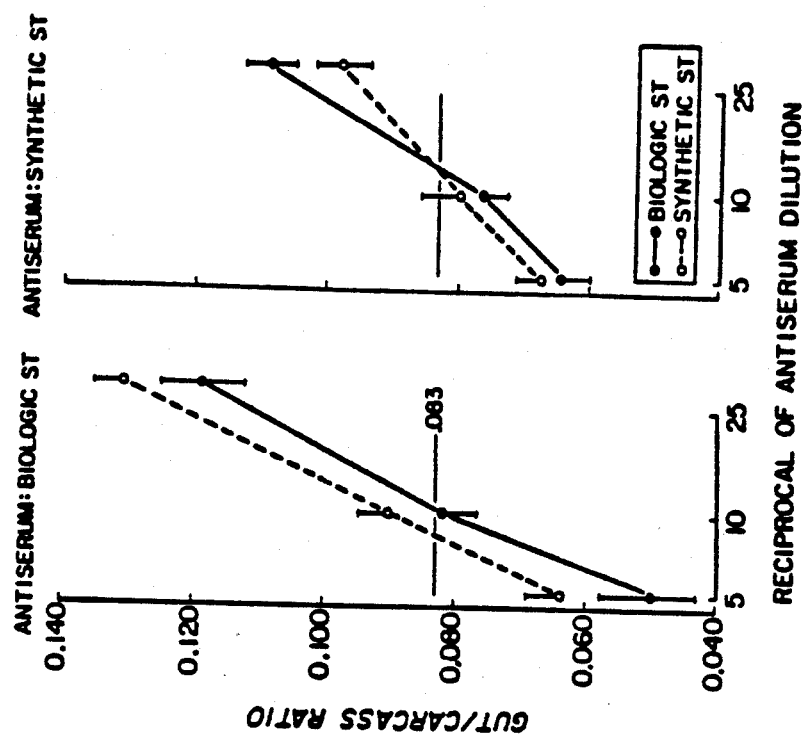

Synthetic heat-stable enterotoxin (ST) embodying the present invention exhibits antigenicity that is at least about 10 percent of that exhibited by biologic ST obtained from *E. coli* which infect humans and other animals. It is known that naturally occurring, biologic ST contains six Cys residues which form three intramolecular disulfide bonds of cystine residues The presence of cystine disulfide bonds has been shown by others, Chan et al., supra., to be necessary for the functioning of naturally ocurring ST.

Two of the six Cys residues of ST may theoretically combine in fifteen different ways to form a disulfide bond of one cystine residue. Six possible combinations of paired Cys residues remain for the formation of a second disulfide bond, and thereafter only one combination is left for the third disulfide bond. Thus, there are a total of ninety (15×6×1) theoretically possible secondary structural isomers of each primary amino acid residue sequence of ST that contains six Cys residues and two or three disulfide bonds.

However, because of the practical difficulty of forming a cystine disulfide bond between pairs of contiguous Cys residues of which there are two pairs in the ST molecule, and redundant possible structures, there are considerably fewer than ninety secondary structural isomers containing two or three disulfide bonds. The specific pairs of Cys residues which form the disulfide bonds present in naturally ocurring ST are not known.

It has now been found that an immunologically active synthetic ST can be prepared having a primary amino acid residue sequence that is substantially the same as that of naturally occurring biologic ST, but whose secondary structure, as determined by disulfide bond formation, is different from that of naturally occurring ST. Immunological activity is found with synthetic ST molecules that contain but one cystine disulfide bond among the pairs of Cys residues present. Enhanced immunological activity is provided to the synthetic ST by formation of two disulfide bonds between two pairs of Cys residues, while maximum immunological activity is provided by the formation of three intramolecular disulfide bonds between three pairs of Cys residues.

A synthetic polypeptide according to this invention includes the amino acid sequence, taken from left to right in the direction from amino-terminus to carboxy-terminus represented by the sequence of Formula I:

$$\overset{R_a^1}{|}\quad \overset{R_b^2}{|} \quad\quad\quad\quad \overset{R_d^4}{|}$$
$$Cys(R_g^7)Cys(R_h^8)GluLeuCys(R_i^9)Cys(R_j^{10})Tyr(Asn)$$
$$\overset{|}{R_c^3}$$

$$\overset{R_e^5}{|} \quad\quad\quad \overset{R_f^6}{|}$$
$$ProAlaCys(R_k^{11})Ala(Thr)GlyCys(R_l^{12})Asn(Tyr)$$

wherein the three specific amino acid residues in parentheses are each an alternative to the immediately preceding amino acid residue in the sequence:

a–f and g–l are integers each having a value of zero or one, whereby if the value of any of a–f or g–l is zero, the corresponding $R_{a-f}^{1-6}$- or $R_{g-l}^{7-12}$-group is absent, while if the value of any one of a–f or g–l is one, the corresponding $R_{a-f}^{1-6}$- or $R_{g-l}^{7-12}$-group is present;

the $R_{a-f}^{1-6}$-groups when taken individually, are the same or different moieties bonded to the sulfur atom of the Cys residue and are selected from the group consisting of hydrogen, an alkyl group containing 1 to about 4 carbon atoms, and a substituted alkyl group containing 2 to about 20 carbon atoms;

$R_{g-l}^{7-12}$ are the same or different alternative amino acid residues to each immediately preceding Cys residue; and at least two of said a–f and two of said g–l are zero whereby the synthetic polypeptide contains at least one intramolecular disulfide bond formed between the at least two Cys residues present In more preferred practice, with reference to the above immunogenic synthetic polypeptide:

"e" is zero when "a" is zero,
"d" is zero when "b" is zero, and
"f" is zero when "c" is zero; and
each of "g" and "k" is zero when "a" is zero,
each of "h" and "j" is zero when "b" is zero, and
each of "i" and "l" is zero when "c" is zero.

The sequence shown in Formula I without the three specific alternative amino acids and subsituent and alternative R-groups corresponds to the carboxy-terminal fourteen amino acid residue sequence of ST Ib and is homologous to amino acids numbered 59–72 of ST Ia. The fourteen amino acids comprising amino acids 59–72 of ST Ia differ from the sequence illustrated above without its alternative amino acids and R-groups at position 65 wherein an asparagine (Asn) residue replaces the tyrosine (Tyr) residue at the position numbered 11 from the amino-terminus of ST Ib, and at position 72 wherein a tyrosine residue replaces the asparagine residue shown.

Thus, the Tyr residue to the immediate right of the fourth Cys residue from the amino-terminus (Tyr-65) may be replaced by the Asn residue that is parenthesized in the above formula. A similar replacement of a Tyr residue for Asn residue may also occur at the carboxy-terminus, as is shown by the parenthesization of the final Tyr residue.

The analogous fourteen amino acid residue sequence from ST Ic is the same as that of ST Ib except for position 69 in ST Ic wherein a threonine (Thr) residue replaces an alanine (Ala) residue of ST Ib. That replacement is also illustrated in the above formula by the parenthesized Thr residue.

It is particularly preferred that at least one of the four amino acid residues present in the eighteen residue ST Ib molecule also be present in the synthetic ST. It is still more preferred that all four of those additional amino acids be present.

The preferred four additional amino acids at amino-terminus of the synthetic ST molecule correspond to amino acid numbers 55 through 58 of ST Ia and are identical to those four amino acids in ST Ib. Three of the four amino acids of ST Ic differ from those of either ST Ia or ST Ib at positions 55 through 58 of ST Ia. Thus, using the above parenthesized alternative naming system, the 4-amino acid polypeptide at the amino terminus of the synthetic ST of Formula I in a most preferred embodiment has a sequence, taken from left to right in the direction from amino-terminus to carboxy-terminus, represented, as shown below in Formula II:

Formula II

Asn(Ser)Thr(Ser)Phe(Asn)Tyr wherein the parenthesized amino acid may replace the immediately preceding amino acid residue.

The synthetic polypeptide contains at least one disulfide bond, more preferably two disulfide bonds and most preferably three disulfide bonds. The disulfide bonds are believed to be formed between the pairs of Cys residues of $R_a{}^1$ and $R_e{}^5$, and $R_b{}^2$ and $R_d{}^4$ as well as $R_c{}^3$ and $R_f{}^6$ when a-f have the value of zero.

However, the Cys residues of $R_a{}^1$ and $R_b{}^2$ as well as those of $R_c{}^3$ and $R_d{}^4$ are adjacent, contiguous pairs. Consequently, synthetic ST polypeptides containing one disulfide bond can have substantially similar secondary structures and antigenicity regardless of whether that single disulfide bond is formed between the Cys residues of $R_a{}^1$ and $R_e{}^5$ or of $R_b{}^2$ and $R_e{}^5$. Similar results pertain to secondary structures formed due to disulfide formation between the Cys residues of $R_a{}^1$ and $R_d{}^4$ rather than $R_b{}^2$ and $R_f{}^6$, and the like.

Thus, the first polypeptide that is synthesized prior to the oxidative formation of an intramolecular disulfide bond contains at least two Cys residues, so the value of at least two of g-l are zero and the corresponding $R_{g-l}{}^{7-12}$ are absent. In view of the similarity of secondary structure that is provided by formation of a disulfide bond between one of two contiguous Cys residues and another Cys residue, a proviso is added that at least one pair of non-contiguous Cys residues from the Cys residues preceding $R_{g-l}{}^{7-12}$ is present. That pair is selected from the group consisting of $R_g{}^7$, $R_h{}^8$ and $R_i{}^9$, $R_j{}^{10}$, $R_g{}^7$, $R_h{}^8$ and $R_k{}^{11}$, and $R_i{}^9$, $R_j{}^{10}$ and $R_l{}^{12}$. In terms of the amino acid residue positions in ST Ib, the pairs of non-contiguous Cys residues are selected from the group consisting of those numbered 5 or 6 and 9 or 10, 5 or 6 and 14, and 9 or 10 and 17 from the amino-terminus of the ST Ib polypeptide.

In addition to its primary amino acid residue sequence, a synthetic ST molecule containing one intramolecular disulfide bond among its six Cys residue is also conveniently characterized by its antigenicity being at least about 10 percent of the antigenicity of biologic ST containing three disulfide bonds. Differences in thin layer chromatographic and electrophoretic mobilities between synthetic ST molecules containing three intramolecular disulfide bonds and biologic ST can also be useful in characterizing synthetic ST molecules containing one disulfide bond when such a synthetic ST can form three intramolecular cystine disulfides.

Since similar pairings of Cys residues other than those that are particularly preferred can also occur for synthetic ST molecules containing two intramolecular disulfide bonds, such ST molecules are also conveniently characterized by having an immunological activity that is at least about 10 percent of that of biologic ST containing three disulfide bonds. Thin layer chromatographic and electrophoritic mobilities are again useful in characterizing synthetic ST molecules containing two intramolecular disulfide bonds when the third disulfide can also be formed.

The antigenicity of a synthetic ST polypeptide as a percentage of the immunogenicity of biologic ST is discussed in detail hereinafter in Section II. Broadly, however, the percentage of antigenicity of a synthetic ST is a relative measure of the amount of anti-biologic ST antibody that recognizes a synthetic ST compared to biologic ST recognized by the same anti-biologic ST antibodies.

Suitable antigenicity has also been found for synthetic ST molecules wherein the sulfur atoms of Cys residues comprise portions of linkages other than cystine disulfide linkages. Because of that fact, the Cys residues of the above sequence of Formula I for synthetic ST are shown as bonded to $R_{a-f}{}^{1-6}$-groups whose identities are discussed hereinbelow.

It is noted however, that because at least one intramolecular cystine disulfide bond is required for immunological activity, and biological activity when that is desired, all six of the $R_{a-f}{}^{1-6}$-groups may not be present in one synthetic ST molecule. Rather, only four of those groups may be present in any one molecule. Thus, for example, where the Cys residues of $R_a{}^1$ and $R_e{}^5$ are combined to form an intramolecular cystine disulfide bond, the values of "a" and "e" are zero (below), the $R_a{}^1$- and $R_e{}^5$-groups are absent and only $R_b{}^2$, $R_c{}^3$, $R_d{}^4$, and $R_f{}^6$ may be present in a synthetic ST molecule.

To account for the presence of one, two or three intramolecular disulfide bonds of cystine residues formed among the six Cys residues, each of the R-groups 1-6 has also been labeled with a subscript letter a-f. Each subscript letter represents an integer having a value of zero or one. For more preferred embodiments, the proviso is added that "e" is zero when "a" is zero, "d" is zero when "b" is zero and "f" is zero when "c" is zero, with the further proviso that at least one of "a", "b" or "c" must be zero whereby a disulfide bond is present between the respective pairs of Cys residues for which one subscript value of zero requires another subscript value to also be zero.

Each of the $R_{a-f}{}^{1-6}$-groups present in the synthetic ST may be hydrogen. In such a case, the Cys residue to which it is bonded is unsubstituted inasmuch as hydrogen is the normal group bonded to the sulfur atom of a Cys residue.

The $R_{a-f}{}^{1-6}$-groups may also be alkyl groups that contain 1 to about 4 carbon atoms. Exemplary of such $R_{a-f}{}^{1-6}$-groups are methyl, ethyl, propyl, i-propyl, n-butyl, i-butyl, and the like.

The $R_{a-f}{}^{1-6}$-groups may further be substituted alkyl groups containing 2 to about 20 carbon atoms wherein the substituents include aryl, substituted aryl, hydroxy, amino, carboxy, carboxamido, halo, substituted vinyl, substituted thio groups, and the like. Exemplary of such substituted alkyl groups are benzyl, alpha-tolyl, 2-hydroxyethyl, 2-hydroxypropyl, 2-aminoethyl, carboxy methyl ($-CH_2CO_2H$), carboxamido methyl ($-CH_2CONH_2$), p-chlorobenzyl, ethylene bis-acrylyl, 2-thioethane carboxy ($-SCH_2CH_2CO_2H$), and the like.

Included among the substituted alkyl groups from which the $R_{a-f}^{1-6}$-groups may be selected is a linking group useful for bonding the synthetic ST to another molecule such as an antigen carrier like the B subunit of an *E. coli* heat-labile (LT) toxin. Exemplary of such linking groups are diacrylates such as ethylene bis-acrylate which can react one double bond with a sulfur atom of a Cys group through a Michael addition reaction while leaving the second double bond free for bonding to a carrier; thioacetic acid, thioproprionic acid, cysteine and N-2-hydroxyethyl-2-thiosuccinimide which can form mixed disulfide bonds with a Cys residue sulfur atom and can react with another molecule such as a carrier through their carboxyl groups, the cysteine amino group or the hydroxyethyl group, respectively.

The $R_{a-f}^{1-6}$-groups may be present separately in a synthetic ST molecule, or mixtures of $R_{a-f}^{1-6}$-groups may be present in one ST molecule. When all of the subscript letters a-f have a value of zero, the $R_{a-f}^{1-6}$-groups are absent, and three intramolecular cystine disulfide bonds are present.

Immunogenicity and biological activity can also be obtained using synthetic ST molecules containing at least one intramolecular cystine disulfide bond between the pairs of Cys residues such as those of $R_a^1$ and $R_e^5$, $R_b^2$ and $R_d^4$, or $R_c^3$ and $R_f^6$, corresponding to the positions numbered 5 and 10, 6 and 14, and 9 and 17 from the amino-terminus of the ST Ib molecule, respectively, when the Cys residues not included in the disulfide bond are replaced by the same or different alternative amino acid residues. The preferred alternative amino acid residues to the Cys residues of Formula I provide no ionic charge to the synthetic polypeptide when the synthetic polypeptide is dissolved in an aqueous solution of physiological pH values.

The alternative amino acid residues to the non-disulfide-bonding Cys groups are illustrated in the above Formula I by the parenthesized groups $R_g^7$, $R_h^8$, $R_i^9$, $R_j^{10}$, $R_k^{11}$ and $R_l^{12}$ each of which can replace the preceding Cys residue, and wherein the subscripts g–l are integers having the value of zero or one. In preferred synthetic ST molecules, if "a" is zero, "g" and "k" are each zero; if "b" is zero, "h" and "j" are each zero; and if "c" is zero, "i" and "l" are each zero.

The amino acid residues Ala and Ser are exemplarly of preferred alternative amino acids that are useful for replacing Cys residues. Biological and immunological activities provided to synthetic ST molecules having Cys residues replaced by Ser residues are illustrated hereinafter.

The above disclosure as to groups $R_a^1$–$R_f^6$ and $R_g^7$–$R_l^{12}$ is equally applicable to synthetic polypeptides containing the fourteen amino acid residues shown in Formula I and to the more preferred synthetic polypeptide containing 18-amino acid residues whose sequence, taken from left to right and in the direction from amino-terminus to carboxy-terminus, is represented by Formula III, below:

Formula III

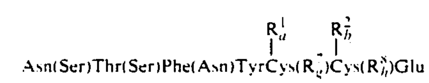

-continued 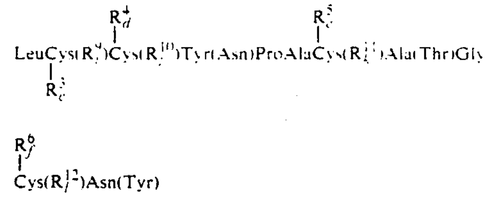 wherein the parenthesized amino acid residues, and $R_a^1$–$R_f^6$ and $R_g^7$–$R_l^{12}$ are as defined hereinbefore.

Both the preferred synthetic polypeptide of Formula I and the more preferred synthetic polypeptide of Formula III may also include an additional group $R_m^{13}$ bonded to the amino-terminal residue of the polypeptide, wherein "m" is an integer having the value of zero or one whereby if the value of "m" is zero, $R_m^{13}$ is absent. If the value of "m" is one, $R_m^{13}$ may be a peptide containing 1 to about 58 amino acid residues, a linking group, and the acyl portion of a carboxylic acid containing 1 to about 20 carbon atoms forming an amide bond with the amino-terminal residue.

When $R_m^{13}$ includes additional amino acid residues bonded to the amino-terminus of the synthetic polypeptide of the fourteen residue polypeptide of Formula I, the additional amino acid residues preferably have the sequence, from the amino-terminus to the carboxy-terminus, shown in Formula II, above.

Addition of the amino acid residue sequence of Formula II to the preferred fourteen amino acid residue sequence provides the sequence of the more preferred eighteen amino acid residue polypeptide of Formula III which itself corresponds to the carboxy-terminal amino acid sequence of ST Ia, ST Ib and ST Ic.

Bonding of 58 or 54 amino acid residues to the fourteen or eighteen residue, synthetic ST polypeptides, respectively, can provide a synthetic polypeptide sequence corresponding to the sequence of native ST Ia or ST Ic. However, since the preferred fourteen, and more preferred eighteen, amino acid sequences of Formulas I and III, respectfully, can provide immunological and biological activities substantially the same as or better than those of the native ST, synthetic polypeptides containing amino acid sequences longer than about the eighteen amino acids of Formula III are not necessary, nor are they desired, with one exception.

The above noted exception is that it can be desirable to include an additional Cys residue at the polypeptide amino-terminus to use as a means of affixing the synthetic polypeptide to another molecule, such as a carrier or a linking group. When used under such conditions, it is convenient to use a sulfur atom blocking group other than a conventional solid phase blocking group lest the added amino-terminal Cys form a cystine disulfide bond with a Cys residue internal to the sequence. One way that a Cys sulfur atom may be blocked during synthesis and selectively deblocked is through the use of an isothiourea analogue of Cys which on cleavage results in the formation of a Cys residue.

The $R_m^{13}$ group may also be linking group in addition to an added Cys residue. Included among such linking groups are the reaction products of the synthetic polypeptide and: (i) omega-amino-monocarboxylic acids containing about 3 to about 6 carbon atoms such as beta-alanine and 6-amino-hexanoic acid, (ii) a dicarboxylic acid or acid chloride or acid anhydride containing about 3 to about 8 carbon atoms such as maleic acid, fumaric acid, succinic anhydride, phthalic anhydride, and the like, (iii) a blocked mercaptan-containing carboxylic acid including 2 to about 4 carbon atoms in the acid chain such as an isothiourea a derivative of thioglycolic or thiopropionic acids, (iv) a dialdehyde containing about 2 to about 8 carbon atoms such as gluteraldehyde or p-phthaldehyde, and the like.

Thus, linking groups containing free amino, carboxyl, mercapto and aldehydo groups can be provided for use in bonding the synthetic polypeptide to another molecule such as a carrier.

$R_m^{13}$ may also be the acyl portion of a monocarboxylic acid containing 1 to about 20 carbon atoms forming an amide bond with the amino-terminal residue of the synthetic polypeptide. Exemplarly of such monocarboxylic acid groups are acetic, propionic, hexanoic, lauric, myristic, stearic, oleic acids, and the like. A long chain fatty acid $R_m^{13}$ group such as stearoyl is usefully bonded to a synthetic ST for passive hemagglutination assays, while short chained $R_m^{13}$ groups such as acetyl bonded to ST provide immunological activities that are slightly reduced compared to the underivatized eighteen residue polypeptide.

The most preferred 18 residue synthetic ST having three intramolecular cyst

After oxidation of the Cys sulfhydryl groups to form the intramolecular disulfide bonds, described hereinafter, there remained no free sulfhydryl groups.

The crude, oxidized polypeptide product was purified by gel filtration on Sephadex G-10 (Pharmacia) and ion exchange chromatography on DEAE-Sephacel (Pharmacia). Amino acid analysis, gel and paper electrophoresis and other chromatographic data all indicated a homogenous product. The overall yield was approximately 25% of theory. Synthetic ST preparations prepared on 5 separate occasions were examined for biologic potency and immunogenicity. All yielded substantially the same responses described herein for the preparation described.

Oxidation Procedure

A first polypeptide having the 18-residue sequence of ST Ib was prepared as discussed above, and had the amino acid sequence, taken from left to right in the direction from amino-terminus to carboxy-terminus, shown in Formula VII, below:

Formula VII

AsnThrPheTyrCysCysGluLeuCysCysTyr-
ProAlaCysAlaGlyCysAsn

This first polypeptide (50 milligrams) was added with gentle agitation to an aqueous 0.1 molar ammonium carbonate-containing solution (pH value 7.8-8.3) to provide a final concentration of 1 milligram of deblocked first polypeptide per milliliter of solution. Continued gentle stirring over a period of 5-15 minutes at room temperature provided a clear solution of the first polypeptide.

Gentle agitation at room temperature was continued for a total period of 8 hours during which time molecular oxygen ($O_2$) in the air was contacted with the solution as oxidizing agent to oxidize the six Cys residues and form three intramolecular cystine disulfide bonds. The loss of free sulfhydryl groups was followed with Ellman reagent [Ellman, *Arch. Biochem. Biophys.*, 82:70-77 (1959)], and was found to be 15%, 40%, 60% and 98% complete at 0.5, 1.5, 2.5 and 8.0 hours, respectively.

The resulting, oxidized polypeptide was collected by lyophilization. It could be used in crude form, but was purified by column chromatography.

The crude material was first passed through a Sephadex G-10 (Pharmacia) column (1.5×80 centimeters) equilibrated with 0.1 molar ammonium acetate. Fractions of 3.5 milliliters/20 minutes were collected with materials being found in fractions 12-15 and 22-28. The contents of these fractions were collected by lyophilization and provided 10 and 36 milligrams, respectively. The material in fractions 22-28 was monomeric synthetic ST as indicated by its elution being in the identical position found by chromatography of biologic ST.

The partially purified synthetic ST could again be used as is, but was purified still further by chromatography on a DEAE-Bio Gel A (Bio Rad, San Raphael, Ca.) column (1.0×25 centimeters). Elution was carried out using a stepwise gradient with the principal amount of material eluting between 50 and 100 millimolar sodium chloride. That material was collected by lyophilization.

The lyophilized material was redissolved in water and desalted on a Sephadex G-25 (Pharmacia) column. The resulting material was collected by lyophilization to yield 28 milligrams of pure, synthetic ST, representing a yield of 56 percent based upon the weight of the crude, first polypeptide. Amino acid analysis of the synthetic ST so prepared gave the following values based on an 18-residue polypeptide (theoretical in parentheses):

| | |
|---|---|
| aspartic acid | 1.93 (2.0) |
| threonine | 1.98 (2.0) |
| glutamic acid | 0.97 (1.0) |
| proline | 1.05 (1.0) |
| glycine | 1.00 (1.0) |
| alanine | 2.00 (2.0) |
| leucine | 1.05 (1.0) |
| tyrosine | 1.89 (2.0) |
| phenylalanine | 0.96 (1.0) |
| cysteine (as cysteic acid) | 5.80 (6.0) |

Figures 1, 2:
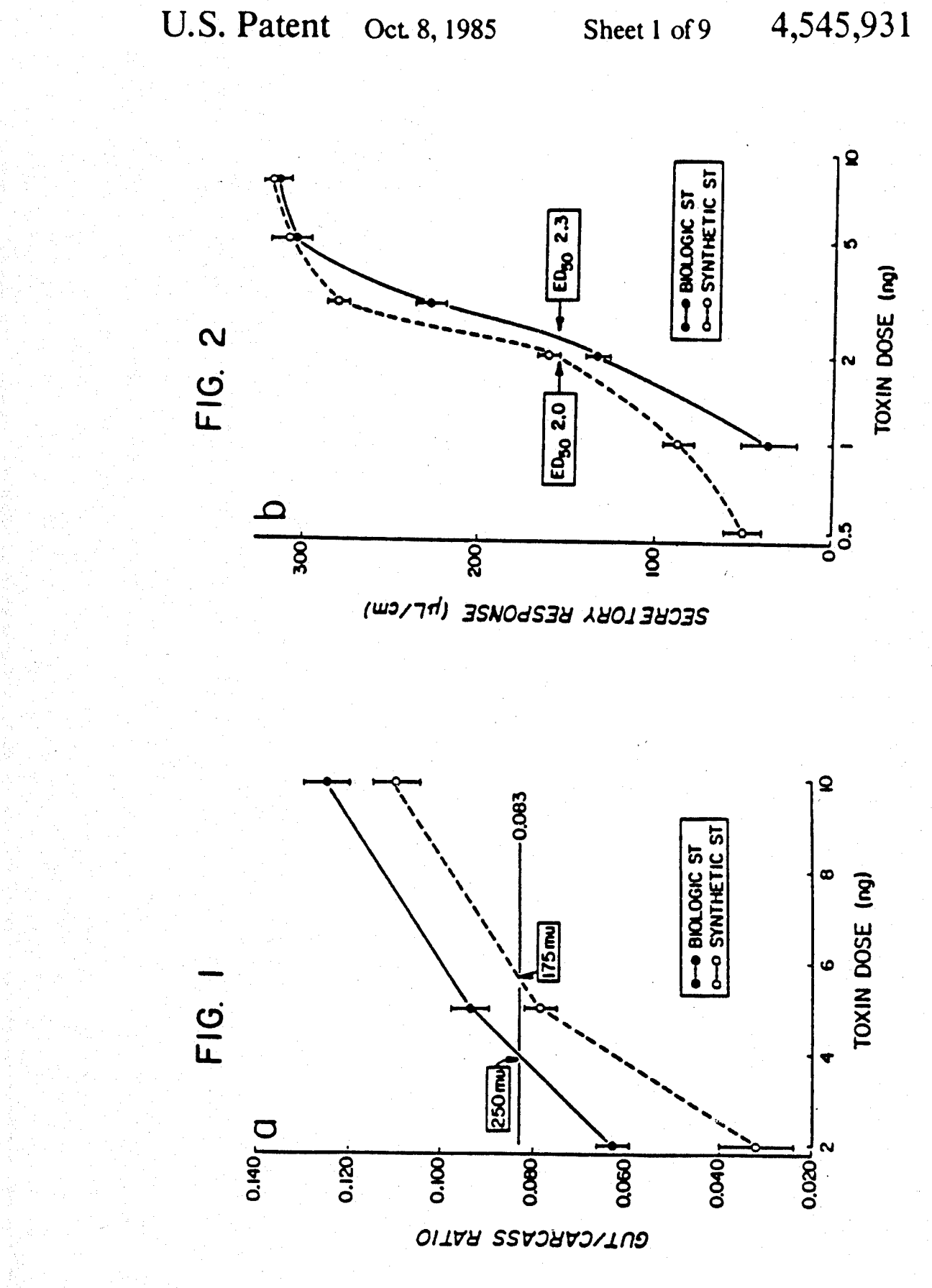

The biological activity of this synthetic ST was determined by the suckling mouse assay of Giannella, *Infect. Immunity*, 14:95-99 (1976), and was found to be substantially the same as biologic ST as is shown in FIG. 1. Substantial identity of secretory responses in ligated ileal loops between synthetic and biologic ST molecules is shown in FIG. 2.

Figure 3:
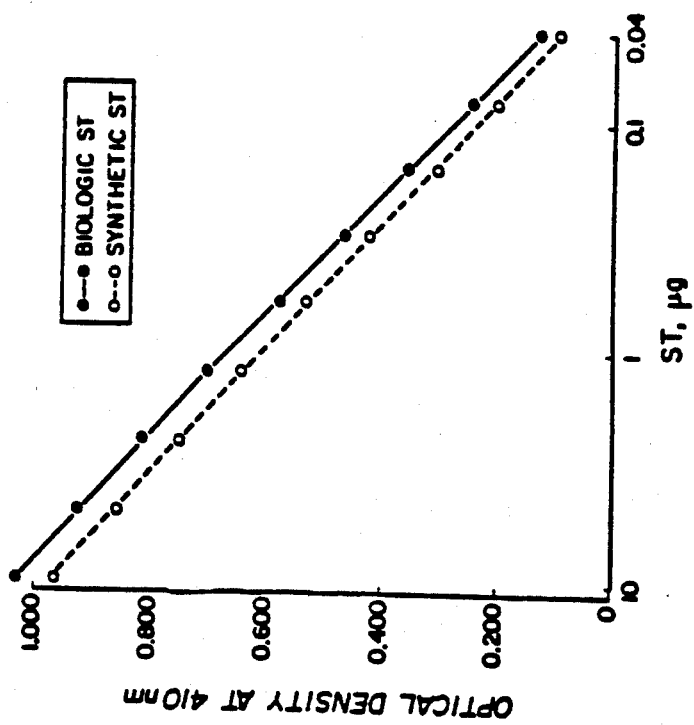

The more important antigenicity of synthetic ST was compared to that of biologic ST by reactivity to antibodies to biologic ST using the ELISA technique of Klipstein et al., *Infect Immunol.*, 37:550-557 (1982). These results are illustrated in FIG. 3 which shows that the antigenicity of the synthetic ST of this preparation was about 70% that of biologic ST. However, FIG. 4 illustrates that seroneutralization on secretory effects by hyperimmune sera were almost identical.

Location of Disulfide Bonds

The three intramolecular disulfide bonds were found to form at different rates. This finding permitted identification of the location of the pairs of Cys residues which combine to form the disulfide bonds.

Thus, further preparations of the above first polypeptide were oxidized under similar conditions and the free sulfhydryl groups were alkylated with iodoacetic acid or idoacetamide at various times during the oxidation reaction. The resulting partially oxidized-partially alkylated polypeptides were then sequenced using a Beckman Sequencer to determine which Cys residues were alkylated at which times during the oxidation reaction. The ratio of alkylated Cys residues at given positions in the partially alkylated-partially oxidized ST compared to the all alkylated-unoxidized ST reflected the location and order of formation of the disulfide bonds.

A ten-fold molar excess of alkylating agent was used over the moles of Cys residue. The oxidation-alkylation reaction mixture was stirred for a period of ten minutes subsequent to the addition of the alkylation reagent, followed by addition of a ten fold excess of dithiothreitol over alkylating agent and a further stirring period of one hour to consume the alkylating agent.

The disulfide bonds in the synthetic ST were found to be formed between the first and fifth, second and fourth, and third and sixth Cys residues from the amino-terminus, those Cys residues correspond to the residues of ST Ib numbered 5 and 14, 6 and 10, and 9 and 17, respectively, from the amino-terminus. These Cys residues also correspond to the Cys residues of $R_a{}^1$ and $R_c{}^5$, $R_b{}^2$ and $R_d{}^4$, and $R^3$ and $R_f{}^6$, respectively whose positions from the carboxy-terminus in the 18-residue polypeptide herein prepared are analogous to the carboxy-terminus positions in the 14-residue polypeptide shown in Formula I.

The rate of formation was found to be in the order of the Cys residues of: $R_b^2$-$R_d^4$ followed by $R_c^3$-$R_f^6$, followed by $R_a^1$-$R_e^5$. Using numbering from the amino-terminus of ST Ib, the order of disulfide bond formation was between the Cys residues numbered 6 and 10, 9 and 17, followed by 5 and 14.

The primary and secondary structure of the synthetic ST so prepared, was from amino-terminus to carboxyl-terminus, therefore:

```
    ┌─────────────────────────┐
 AsnThrPheTyrCysCysGluLeuCysCys
           ┌──┘         │
  TyrProAlaCysAlaGlyCysAsn
``` wherein the lines connecting the Cys residues represent the disulfide bonds formed between those residues.

The rate of disulfide bond formation as a function of pH value using the above human ST first polypeptide, oxidation with molecular oxygen contacted with a gently stirring solution containing 1 milligram per milliliter of the first polypeptide is shown below:

| pH value | Moles of —S—S—formed/hour |
|---|---|
| 5.0 | 0.30 |
| 6.0 | 0.45 |
| 7.0 | 0.90 |
| 8.0 | 1.50 |
| 9.0 | 1.20 |
| 10.0 | 0.75 |

Stirring speed and temperature also effect the rate of oxidation. Increases in either or both provide a more rapid rate of oxidation and disulfide bond formation.

Comparison of Physical Properties of Synthetic and Biologic ST

Thin layer chromatography using cellulose coated plastic sheets (Eastman) and a solvent of butanol:acetic acid:water (200:30:75 parts by volume, respectively) provided an $R_F$ value of 0.307 for the above prepared synthetic ST having three disulfide bonds. Staples et al., supra, reported an $R_F$ value of 0.8-0.9 using the same solvent system and cellulose coated glass plates (Eastman).

Paper electrophoresis at pH 2.1, 500 volts for 90 minutes at room temperature provided an $R_F$ value of 0.80 relative to lysine for the above synthetic ST. Staples et al., supra, using thin layer electrophoresis on cellulose at pH 1.9 reported a mobility that was about the same as that of glutamic acid. Conversion of glutamic acid mobility under the Staples et al. condition to that of lysine under the conditions used for the synthetic ST provides a relative $R_F$ of 0.50.

Preliminary results from optical rotatory dispersion determinations using the above synthetic ST and its biologic counterpart showed that the two molecules are different.

Synthetic ST Molecules Containing Two Disulfide Bonds

Synthetic 18-residue polypeptides analogous to human ST Ib molecules were prepared in a manner substantially the same as that described above, except that pairs of Cys residues were replaced in the first polypeptide and resulting, oxidized, ST molecules by alternative $R_g^7$-$R_l^{12}$-groups which provide no ionic charge to the synthetic ST polypeptide when that polypeptide is dissolved in aqueous solution at physiological pH values. The synthetic ST molecules so prepared were then assayed for their immunuological and biological activities. The $R_g^7$-$R_l^{12}$-groups used in these determinations were the amino acid serine (Ser).

The first polypeptide from which these synthetic ST Ib analogues were prepared had the amino acid sequence, taken from left to right in the direction from amino-terminus to carboxy-terminus, shown in Formula VIII, below:

Formula VIII

AsnThrPheTyrCys($R_g^7$)Cys($R_h^8$)GluLeuCys($R_i^9$)-Cys($R_j^{10}$)TyrProAlaCys($R_k^{11}$)AlaGlyCys($R_l^{12}$)Asn wherein each of the $R_{g-l}^{7-12}$-groups were alternative Ser residues to the immediately preceding Cys residue.

For this group of immunological assays as well as for all of the other such assays, the haptenic synthetic ST Ib and biologic ST Ib molecules were first coupled to a carrier in substantially the same amounts and under substantially the same conditions, as discussed in Section IV, hereinafter. Antisera were then raised to the antigens so produced. The abilities of those two antisera to recognize each of the ST molecules were measured and compared by the above-discussed ELISA technique. Recognitions of the synthetic ST and biologic ST by their own antisera were set at 100% and the amounts of recognition for each of the other ST molecule was then calculated accordingly. The suckling mouse assay was used for determining biological activity.

Thus, for these comparative determinations, pairs of $R_g^7$-$R_l^{12}$ were utilized in which the value of four of g-l 1 was zero, while the value of two of g-l was one. The pairs of alternative $R_g^7$-$R_l^{12}$-groups utilized were those whose preceding pairs of Cys residues are shown in Formula I for the 14-residue polypeptide to be bonded to the groups $R_a^1$ and $R_e^5$, $R_c^3$ and $R_f^6$, and $R_b^2$ and $R_d^4$. These groups correspond to the Cys residues numbered 5 and 10, 6 and 14, and 9 and 17, respectively, from the amino-terminus of the ST Ib amino acid sequence. The $R_g^7$-$R_l^{12}$-groups for which g-l were one were therefore $R_g^7$ and $R_k^{11}$, $R_i^9$ and $R_l^{12}$, and $R_h^8$ and $R_j^{10}$, respectively, of the amino acid sequence of Formula VIII. The results for these comparisons are shown in Table 1 below along with standards of biologic ST Ib, the above-prepared synthetic ST Ib and porcine ST Ia.

TABLE 1

Relative Immunogenical and Biological Activities

| ST Assayed | Anti-Syn. ST[1] (Percent) | Anti-Biol.-ST[2] (Percent) | Suckling Mouse (Percent) |
|---|---|---|---|
| $R_g^7$ + $R_k^{11}$ Ser | 45 | 62 | 66 (8.2 ng[3]) |
| $R_i^9$ + $R_l^{12}$ Ser | 21 | 43 | 46 (12.0 ng[3]) |
| $R_h^8$ + $R_j^{10}$ Ser | 41 | 74 | 92 (6.0 ng[3]) |
| Biologic Ib | 35 | 100 | 100 (5.7 ng[3]) |
| Synthetic Ib | 100 | 263 | 120 (5.3 ng[3]) |

TABLE 1-continued
Relative Immunogenical and Biological Activities

| ST Assayed | Assay Anti-Syn. ST[1] (Percent) | Anti-Biol.-ST[2] (Percent) | Suckling Mouse (Percent) |
|---|---|---|---|
| Porcine Ia | 3 | 450[4] | 10 (55 ng[3]) |

[1] Percent recognition of assayed ST by antiserum raised to synthetic ST
[2] Percent recognition of assayed ST by antiserum raised to biologic ST
[3] Nanograms required to provide a gut: whole body ratio of 0.083
[4] This value appears to be anomolously high by a factor of about 1.5 to about 2.

The results in the above Table illustrate several features of the present invention. First, substantial immunologic activity can be obtained without the presence of three disulfide bonds in the ST molecule. Second, and a related feature, all of the Cys residues are not needed and some may be replaced by other amino acid residues. Third, biological activity which can lead to diarrhea in a vaccinated animal can be reduced while substantial immunological activity is maintained.

A fourth feature of this invention that the above results illustrate is that the biologic ST Ib molecule and the synthetic ST Ib molecule containing three disulfide bonds are immunologically different entities, thereby underscoring the before-noted differences in chromatographic, electrophoretic and optical rotary dispersion chracteristics of the two molecules. Thus, antibodies to biologic ST recognized the synthetic ST 263% better than they recognized the biologic ST to which they were raised. Similarly, antibodies raised to the synthetic ST recognized biologic ST only 35% as well as they recognized the synthetic ST.

The difference between the synthetic and natural ST molecules is further underscored by the ST Ia (porcine) which was hardly recognized by antibodies to the synthetic ST, but was recognized about 10- to about 100-times better by antibodies raised to biologic ST than was biologic ST itself, taking into account the fact that the 450% value may be anomolously high. Even if the value of 450% is too high by a factor of about 5, the antibodies raised to biologic ST Ib recognized porcine ST Ia at least about 20-times better than did antibodies to the synthetic ST Ib. If the biologic and synthetic ST Ib molecules were the same, antibodies to each would be expected to recognize the porcine ST Ia with about the same efficiency. Since that was decidely not the case, the biologic ST Ib and synthetic ST Ib molecules must be different although both contain identical primary amino acid sequences and both contain three intramolecular disulfide bonds.

Other Preparations

Additional first polypeptides and ST molecules have been prepared (i) via different oxidation routes, (ii) having different amino acid sequences from the ST Ib, (iii) replacements of different $R_{g\text{-}j}^{7\text{-}12}$-groups, (iv) alkylated Cys $R_{a\text{-}f}^{1\text{-}6}$-groups and (v) $R_m^{13}$ groups bonded to the N-terminal amino acid residue of the 18-residue ST Ib molecule. Many of these materials have been assayed for immunological and/or biological activities by the above suckling mouse and ELISA techniques using antisera to the synthetic ST prepared in (3), below. The results of several of these preparations and assays are listed below in Table 2.

TABLE 2
Other Preparations

| | ELISA[2] (Percent) | Suckling Mouse (Percent) |
|---|---|---|
| Oxidations[1] | | |
| (1) Room temperature: 1.0 mg/ml; 0.1 M NH$_4$HCO$_3$; pH 8.0; 6 hrs. | 95 | 120 (5.3 ng) |
| (2) 4° C.; 1.0 mg/ml; 0.1 M NH$_4$HCO$_3$; pH 8.0; 6 hrs. | 87 | 80 (6.9 ng) |
| (3) Room temperature: 1.0 mg/ml; 0.1 M NH$_3$; pH 10.3; 1.0 hr.; lyophilized; 4° C.; 1.0 mg/ml; buffered saline; pH 7.2; 8 hrs. | 27 | 35 (6.5 ng) |
| (4) Room temperature: 1.0 mg/ml; 0.1 M NH$_3$; pH 10.3; adjusted with acetic acid to pH 8.0 after 5 minutes; 1 equivalent K$_3$Fe(CN)$_6$; 3 hrs. | less than 2 | N.D.[4] |
| (5) Room temperature: 2.0 mg/ml; 0.1 M NH$_3$; pH 10.3; 1 hr.; lyophilized; 4° C.; 2.0 mg/ml; buffered saline; 8 hrs. | 13 | 55 (10 ng) |
| (6) Room temperature: 1.0 mg/ml; 1.0 mg/ml; performic acid | much less than 1 | N.D. |
| (7) Room temperature: 1.0 mg/ml; 0.1 M NH$_3$; pH 10.3; adjusted immediately upon solution with acetic acid to pH 8.0; 22 hrs. | 53 | N.D. |
| (8) Room temperature: 1.0 mg/ml; 0.1 M NH$_3$; pH 10.3; 22 hrs. | 26 | N.D. |
| (9) Room temperature: 1.0 mg/ml; 0.1 M NH$_4$HCO$_3$; pH 8.0; 8 hrs.; Sephadex G-10 and DEAE-Bio Gel A; lyophylize. | 100 | N.D. |
| (10) Room temperature: 1 mg/ml; 8 M urea; pH 8.0; 8 hr. | 7 | N.D. |
| Alkylation | | |
| (11) Oxidize as per (1); alkylate with average of 4 moles iodoacetic acid after an average of one disulfide formed. | 12 | N.D. |
| (12) Oxidize as per (1); alkylate with average of 2 moles of iodoacetic acid after an average of two disulfides formed. | 14 | N.D. |
| Acyl ST ($R_m^{13}$) | | |
| (13) An N—acetyl group was added to the amino-terminus of the 18-amino acid residue of the first polypeptide prior to removal of the peptide blocking groups, followed by deblocking and oxidation as in (7). | 53 | N.D. |
| Alternative sequences | | |
| (14) Carboxy-terminal 14 amino acids of ST Ib, oxidized as per (9). | N.D. | N.D. |
| (15) Carboxy-terminal 15 amino acids of ST Ib, oxidized as per (9). | N.D. | N.D. |
| (16) Cys residues preceding Formula VIII $R_h^8$ and $R_i^9$ replaced by Ser, oxidized as per (9). | N.D. | N.D. |
| (17) Cys residues preceding Formula VIII $R_i^9$ and $R_k^{11}$ replaced by Ser, oxidized as per (9). | N.D. | N.D. |
| (18) Cys residues preceding Formula VIII $R_j^{10}$ and $R_k^{11}$ | N.D. | N.D. |

TABLE 2-continued

Other Preparations

|  | ELISA[2] (Percent) | Suckling[3] Mouse (Percent) |
|---|---|---|
| replaced by Ser, oxidized as per (9). | | |

A first polypeptide corresponding to the sequence of Formula VIII wherein g-l were zero was used for each of (11)-(13). First polypeptides corresponding to the KST Ib carboxy-terminal 14-amino acids and 15-amino acids were used in (14) and (15), respectively. First polypeptides corresponding to the noted substitutions to the sequence in Formula VIII were used for (16)-(18) and were then oxidized. Reaction conditions are provided in the order of temperature; concentration of first polypeptide in milligrams/milliliter; molar concentration of added ingredients; pH value at which oxidation was initiated; and duration of the oxidation procedure. Each solution was stirred gently to contact the solution with atmospheric molecular oxygen as oxidizing agent, unless otherwise specified.
[2]The ELISA was conducted as per Table 1 with antisera raised to the ST prepared in (3) as the basis for comparisons.
[3] The suckling mouse assay was conducted as per Table 1 with percentages being based upon the value for biologic ST, the values in parentheses being nanograms of ST providing a gut: whole body ratio of 0.083.
[4] N.D. = Not determined.

The above results illustrate that the highest immunological activity is achieved under oxidation conditions in which the first synthetic polypeptide is present in solution at a concentration of less than about 2 milligrams per milliliter, oxygen in the air is the oxidizing agent, the pH value is below about 10, the temperature of the reaction is about zero to about 25° C. and the oxidation reaction time is less than about 24 hours.

General Synthetic Procedure

A general synthetic procedure for preparing a synthetic ST molecule having at least about 10 percent of the antigenicity of biologic ST based upon the above results and several other determinations is as follows:

(1) A first synthetic polypeptide is prepared in the substantial absence of oxidizing agent. The first synthetic polypeptide includes the amino acid residue sequence of Formula V or Formula VI and is free from any intramolecular, cystine disulfide bonds.

(2) The first polypeptide so prepared is dissolved in aqueous solution at a concentration of less than about 2 milligrams per milliliter and more preferably at a concentration of about 1 milligram per milliliter, or less. The pH value of the solution into which the first polypeptide is dissolved is about 7.5 to about 10.5.

(3) The first polypeptide-containing solution is thereafter contacted with molecular oxygen in the air as an oxidizing agent. The pH of the solution during oxidation is preferably about 7.0 to about 9.5, and more preferably about 7.5 to about 9. The solution is preferably contacted with the oxidant by gentle stirring.

(4) Contact between the solution and the air is maintained for a period of about 1 to about 24 hours, and more preferably for about 2 to about 8 hours, to form at least one intramolecular disulfide bond between at least two of the Cys residues present. In preferred practice, the disulfide bond is formed between the Cys residues preceding the pairs $R_g^7$ and $R_k^{11}$, $R_h^8$ and $R_j^{10}$, and $R_i^9$ and $R_l^{12}$ of Formulas V or VI, which correspond to the positions of the residues numbered 5 and 10, 6 and 14, and 9 and 17 from the amino-terminus of the ST Ib molecule, respectively. In more preferred practice, contact between molecular oxygen and the solution is maintained for a period sufficient to form two disulfide bonds, preferably between the above-mentioned pairs of Cys residues, and still more preferably for a period sufficient to form three disulfide bonds, again preferably between said pairs of Cys residues.

The oxidation is preferably carried out at a temperature of about 0° C. to about 25° C.

(5) Upon completion of the oxidation reaction, the synthetic ST may be collected as by lyophilization and purified if desired.

III. Uses of Synthetic ST

The synthetic as discussed above was linked to a carrier molecule or used alone in determinations carried out under the direction of Dr. Frederick A. Klipstein of the University of Rochester Medical Center, Rochester, N.Y. The results of experimental determinations and the procedures for carrying out these determinations are discussed herein and in Section IV, hereinafter.

A. Properties

ST Ib purified to homogeneity from human *E. coli* $LT^-/ST^-$ strain 18D (042:H47) has an estimated molecular weight of 1,972 and consists of ten different amino acids arranged in a sequence of 18 amino acids [Staples et al., supra] whose primary structure was shown by Chan et al., supra, to be AsnThrPheTyrCysCysGluLeuCysCysTyrProAlaCysAlaGlyCysAsn. A synthetic molecule with this primary structure was prepared (Section II) and the biological properties of this polypeptide were compared with that of pure ST obtained by bacterial growth of strain 18 D (biologic ST).

Capacity To Induce Fluid Secretion

Synthetic and biologic ST were substantially equally potent in their ability to induce fluid secretion in the suckling mouse assay (FIG. 1) and rat ligated ileal loops (FIG. 2). The slight variations observed in the minimum effective dosages of the two toxins in each assay model were within the range of experimental variation, and, in fact, several subsequently prepared preparations of synthetic ST evoked an identical response to that of native or biologic ST in the suckling mouse assay. Exposure to 100° C. for 30 minutes did not affect the potency of either toxin in either animal assay system.

Previous observations have shown that destruction of the disulfide bridges of biologic ST by treatment with reducing reagents such as 2-mercaptoethanol or dithiothreitol abolished its biologic activity, Staples, et al., supra. Exposure of synthetic ST to $5\times10^{-4}$ molar dithiothreitol for 60 minutes also abolished its secretory activity in the suckling mouse assay.

Immunological Relationship

The antigenicity of synthetic and biologic ST was similar when each was tested by enzyme linked immunosorbent assay (ELISA) using hyperimmune antisera to biologic ST. When those concentrations which yielded an optical density of 0.600 at 410 nanometers were compared, the antigenicity of synthetic ST was observed to be 70% that of biologic ST (FIG. 3), but the antigenicity of the toxins was identical when both were tested using hyperimmune antisera to synthetic ST. These results were substantially improved in later preparations as illustrated in Table 1, above, with the synthetic ST being about 3-fold better than biologic ST Ib in this same ELISA assay.

In order to evaluate the neutralizing effect of hyperimmune antisera to either synthetic or biologic ST on the secretory effect of the toxins in the suckling mouse assay, three mice for each datum point were given 100 microliters intraintestinally containing 2 mouse units (MU), twice the minimum effective dosage (see Materials and Methods Section) of each toxin that had been incubated with the designated antiserum dilution for 3 hours at 37° C. (FIG. 4). The number of mouse units neutralized by 1 milliliter of antiserum was derived from multiplying the projected antiserum dilution required to neutralize (i.e., yield a gut:carcass ratio of at least 0.083) the secretory effect times the 10-fold dilution factor times the factor of 2 in order to adjust for the 2 mouse units used.

Hyperimmune antisera to each of the toxin preparations seroneutralized the secretory effect in the suckling mouse assay of synthetic and biologic ST to the same approximate degree: one milliliter of hyperimmune rabbit antiserum to biologic ST neutralized 160 MU of synthetic and 190 MU of biologic ST, while one milliliter of goat hyperimmune antiserum to synthetic ST neutralized 220 MU of synthetic and 240 MU of biologic ST.

Immunization of Rats

Immunization with the synthetic ST yielded serum antitoxin titers of 1:32 (four-fold greater than that of the controls) and mucosal IgA titers of 1:64 (fivefold greater than that of the controls). Fluid secretion was reduced by a significant degree that was comparable to an amount previously observed in rats immunized with semipure biologic ST (Klipstein, et al., supra) in rats challenged with either synthetic or biologic ST and with the viable ST-producing strain (Table 3), below.

TABLE 3

| ST immunogen | Results Of Challenge In Immunized Rats Challenge[d] | | |
|---|---|---|---|
| | ST(B) toxin | ST(S) toxin | LT−/ST+ |
| Synthetic (S) | 54 ± 2 | 66 ± 2 | 55 ± 1 |
| Biologic (B)[b] | 83 ± 9 | ND[c] | 69 ± 2 |

[d]Mean ± standard error of the mean percent reduced secretion in immunized rats as compared to similarly challenged unimmunized animals
[b]Data taken from Klipstein et al., supra.
[c]Not determined.

The above results show that immunization with a synthetically-produced ST toxin whose structure is based on that of human ST provides protection against challenge with ST-producing enterotoxigenic strains of *E. Coli* of human origin.

B. ST-LT Conjugates

The results discussed in this section relate to conjugate compositions and their properties obtained by cross-linking, under various conditions, synthetic ST (Section II) to either the LT holotoxin or its nontoxic component, the B subunit as a carrier which is responsible for binding of the toxin to specific receptors on the mucosal surface. The efficacy of a vaccine consisting of synthetic ST cross-linked to the B subunit for arousing specific serum and mucosal antitoxin responses to each of the component toxins is also demonstrated, thus providing strong protection in immunized rats against challenge with either toxin form or heterologous viable ETEC which produce either ST or LT.

Conjugation of ST to LT

Figure 5:
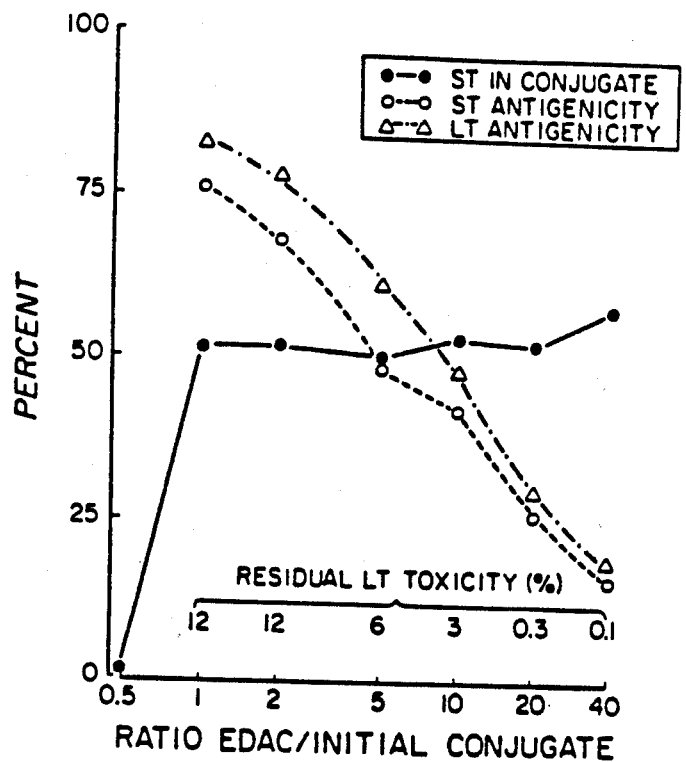

Synthetic ST was conjugated to the LT holotoxin from an initial molar ratio of ST to LT of 100:1 using ratios of 1-ethyl-3-(3-dimethylaminopropyl) carbodiimide (EDAC) to total conjugate protein which varied between 0.5:1 to 40:1 (FIG. 5). Coupling of the maximum amount of ST to LT occurred at an EDAC to conjugate ratio of 1:1; however, an unacceptable degree of residual LT toxicity persisted at this ratio. Increasing the EDAC to conjugate protein ratio resulted in a progressive decrease in residual LT toxicity but this was accompanied by a corresponding reduction in the antigenicity of both toxins in the conjugate.

An EDAC to conjugate ratio of 20:1 resulted in a conjugate with an acceptable degree of reduced LT toxicity (0.3%), but the antigenicity of both component toxins was reduced to less than 25% at this ratio, indicating that this conjugate would be an ineffectual immunogen. These observations led to substitution of the nontoxic B subunit for LT, thereby circumventing the problem of residual LT toxicity.

Conjugation of ST to B Subunit

Synthetic ST was conjugated to B subunit from an initial molar ratio of ST to B subunit of 100:1, using EDAC to conjugate protein ratios which varied between 0.5:1 and 40:1. The pattern of ST incorporation and the changes in antigenicity were similar to those noted for ST conjugation to LT except that the maximum amount of ST was coupled at an EDAC to conjugate ratio of 2:1. The toxicity of the conjugate obtained at this ratio was confined to that of the ST present; it was reduced to 0.3% of unattenuated toxin.

Figure 6:
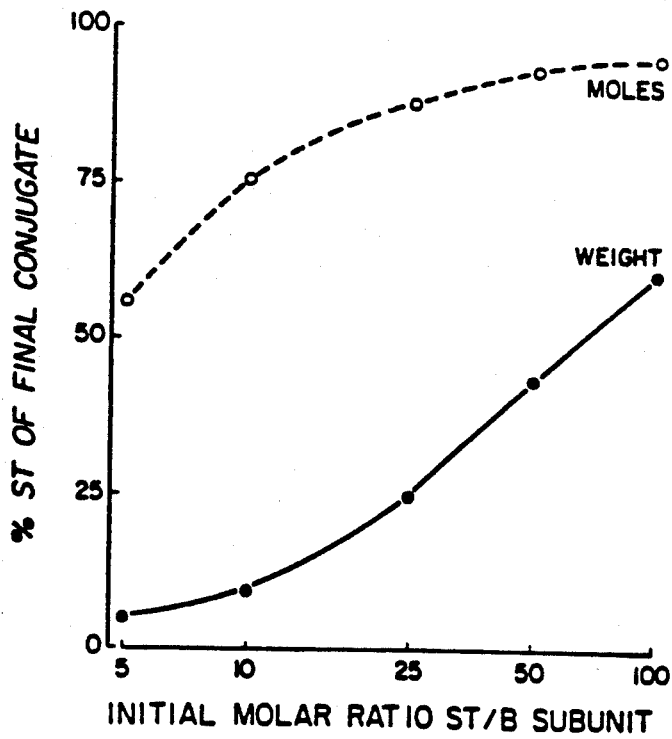

An EDAC to conjugate ratio of 2:1 was employed, therefore, in studies which utilized radiolabelled ST to determine the influence of the initial molar ratio of ST to B subunit on the amount of ST incorporated into the conjugate. Ten nanomoles of ST (5 nanomoles of cold, unlabelled ST plus 5 nanomoles of radiolabelled ST) were mixed with from 2 to 0.1 nanomoles of B subunit yielding initial ST to B subunit molar ratios of from 5:1 to 100:1 (FIG. 6). Increasing the initial ST to B subunit ratio resulted in progressively greater amounts of ST coupled to the B subunit. Although an initial ST:B subunit ratio of 25:1 yielded a final conjugate which contained more than 90% ST on a molar basis, the proportion of ST was only 25% on a weight basis; the latter value increased when larger initial molar ratios were used.

Antigenicity of the Conjugates

Figure 7:
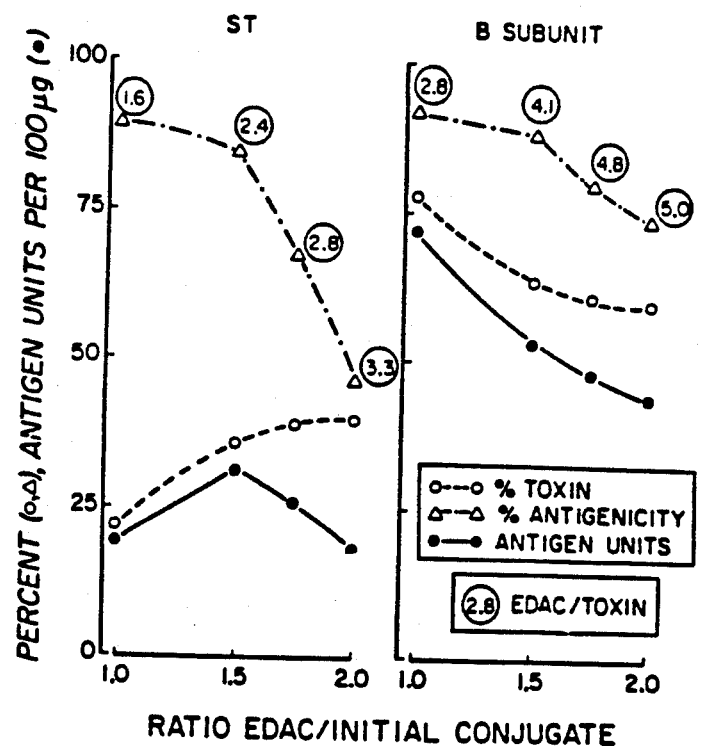

The effect of the EDAC concentration on the composition and antigenicity of the individual toxins in the final conjugates was assessed by conjugating a 50:1 molar ratio of ST to B subunit using EDAC to conjugate ratios which varied between 1:1 and 2:1 (FIG. 7). Maximum conjugation of ST occurred at an EDAC to conjugate ratio of 2:1; however ratios of greater than 1.5:1 resulted in a precipitous fall in ST antigenicity and a moderate decline in B subunit antigenicity. The maximum number of ST antigen units (derived by multiplying the percentage of toxin present times the percentage of its antigenicity) was achieved at an EDAC to conjugate ratio of 1.5:1.

Figure 8:
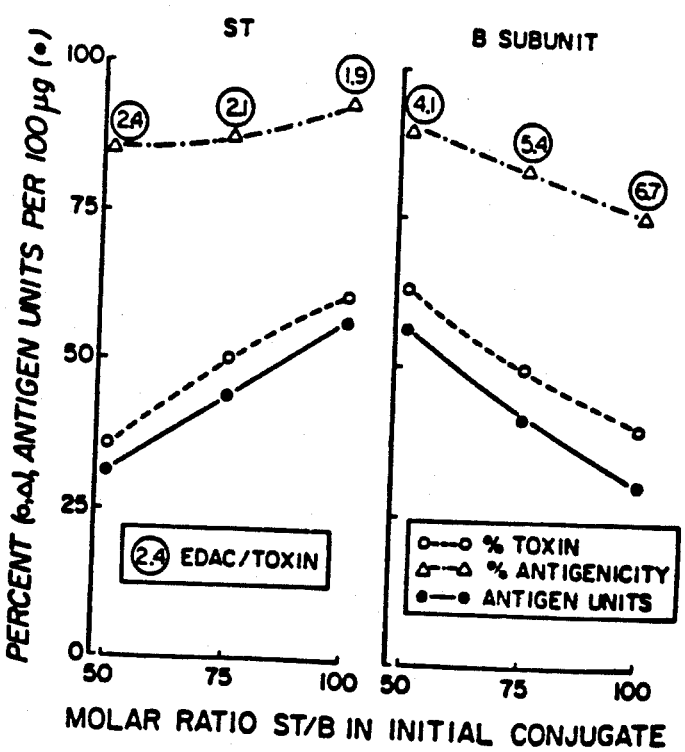

An EDAC to conjugate ratio of 1.5:1 was used, therefore, in studies which determined the effect of the initial molar ratio of ST to B subunit on the composition and properties of the final conjugate. Increasing the initial molar ratio of ST to B subunit from 50:1 to 100:1 resulted in a progressively greater proportion of ST in the final conjugate (FIG. 8).

Since changes in the initial molar ratio were achieved by keeping the amount of ST (300 nanomoles) constant and reducing the amount of B subunit added (from 6 to 3 nanomoles), the ratio of EDAC to ST decreased while the ratio of EDAC to B subunit rose as initial molar ratios increased. This change accounted for the fact that the ST antigenicity rose slightly while that of the B subunit fell moderately. The net effect of these two factors (composition and antigenicity) was that increasing the initial molar ratio resulted in progressively greater amounts of ST antigen units, with a corresponding fall in B subunit antigen units, in the final conjugate.

Properties of The Vaccine Used For Immunization

It was previously shown that the B subunit is a weaker immunogen than the LT holotoxin on a molar basis [Klipstein et al., *Infect. Immun.*, 31:144–150 (1981)] and preliminary studies indicate that it is a weaker immunogen in terms of antigen units than either the LT holotoxin or synthetic ST. This led to selection of a vaccine which contains more B subunit than ST antigenicity.

The immunogen was produced by conjugating an initial ST to B subunit molar ratio of 50:1 using an EDAC to conjugate ratio of 1.5:1. The conjugate contained 36% (by weight) ST which had 85% retained antigenicity and 0.13% persistent toxicity, and 64% (by weight) B subunit which retained 89% of its antigenicity. When tested directly (i.e., in samples not adjusted to contain 100% of each toxin), the vaccine contained 37 ST and 59 B subunit antigen units per 100 micrograms and had a residual ST toxicity of 0.06%.

Results of Immunization

Rats immunized with the above vaccine were given 1,000 micrograms primary immunization by the intraparenteral (i.p.) route followed by the two 3,000 microgram peroral (p.o.) boosts. Previous studies have shown that in rats immunized with LT by this approach, the degree of the antitoxin response and of protection correlate with the total p.o. dosage [Klipstein et al., *Infect. Immunol.*, supra; Klipstein et al., *Infect. Immunol.*, 37:1086–1092 (1982); Klipstein et al., *Infect Immunol.*, 31:252–260 (1981)]. This immunization schedule amounted to 2,200 ST and 3,450 B subunit antigen units.

Serum IgG antitoxin titers to ST were increased 4-fold and those to the B subunit were increased 5-fold over values in control, unimmunized rats. Mucosal secretory IgA antitoxin titers to both ST and B subunit were 7-fold greater in immunized rats than in controls. Immunized rats were significantly protected against challenge with LT or with either synthetic or biologic ST as well as against heterologous viable organisms which produce these toxins either singly or together as shown in Table 4, below.

TABLE 4

Results of Challenge in Rats Immunized With
Cross-Linked ST-B Subunit Vaccine
% Reduced Secretion After Challenge With[a]

| LT toxin | LT=/ST− | LT=/ST− | ST(B) toxin[b] | ST(S) toxin[b] | LT−/ST− |
|---|---|---|---|---|---|
| 94 ± 3 | 61 ± 2 | 68 ± 2 | 97 ± 3 | 78 ± 1 | 76 ± 2 |

[a]Values are the mean ± standard error of the mean. Reduced secretion of more than 50% represents a significant (P less than 0.001) difference between immunized and unimmunized rats.
[b]ST(B) signifies biologic ST, and ST(S) signifies synthetic ST.

The above findings that synthetically produced pure ST can be used to provide an effective, nontoxic immunogen when it is cross-linked to the LT toxin B subunit surmounts a major obstacle in the development of a safe, practical vaccine that provides protection against ETEC strains which produce either the ST or LT form of toxin. Previous results showed that cross-linking a semipure preparation of biologic ST to LT yielded an immunogen in which the ST acquired immunogenicity as a function of coupling to the large molecular weight LT molecule, and in which, under the proper conjugation conditions, most of the antigenicity of the component toxins was maintained while their toxic properties were greatly reduced [Klipstein et al., *Infect. Immunol.*, 37:550–557 (1981)].

Although that vaccine with biologic ST provided strong protection in immunized animals against challenge with ETEC strains which produce either toxin form, the heterogeneous composition of the semipure ST toxin component clearly precluded its adoption for human use. The complicated and tedious methodology involved in processing biologic ST to total purity renders large scale, much less commercial scale, production of this material difficult. The above findings indicate that synthetically-produced ST, which can readily be made in large quantities, provides an equally effective vaccine.

The reaction conditions for conjugates derived from synthetic ST which yield maximal incorporation of ST with the carrier together with optimal properties in terms of residual antigenicity and toxicity differ from those previously observed for conjugation of semipure biologic ST to LT. In both circumstances, (1) a critical amount of the conjugating reagent carbodiimide was necessary for coupling the maximum amount of ST to the carrier, (2) the proportion of ST present in the final conjugate was dependent on the initial molar ratio of ST mixed with LT, and (3) increasing the ratio of carbodiimide to either toxin in the conjugate resulted in a progressive decline both in the antigenicity and in toxicity of the cross-linked toxins. In the case of semipure biologic ST, conjugation conditions were identified which yielded a conjugate with maximal incorporation of ST to LT and at the same time retained most of the antigenicity but markedly reduced the toxicity of both of the cross-linked toxins.

Such did not occur, however, when synthetic ST was conjugated to LT. Maximum coupling of synthetic ST to LT occurred at a much lower carbodiimide to conjugate ratio under which conditions the residual LT toxicity of this conjugate was unacceptably high. A reduction in LT toxicity to acceptable levels was achieved only at carbodiimide to toxin ratios which severely compromised the antigenicity of both of the cross-linked toxins. These findings led to circumventing this problem by substituting the nontoxic B subunit for the LT holotoxin as the carrier.

The proportion of antigenicity (expressed as antigen units) for each of the component toxins present in the final conjugate derived by cross-linking synthetic ST to the B subunit can be altered by varying the conditions of the conjugation reactions. Thus, in the presence of the proper concentration of carbodiimide, a low initial molar ratio of ST to B subunit yielded a conjugate with predominantly ST antigenicity whereas a high initial molar ratio yielded one in which B subunit antigenicity is greatest.

Preliminary observations suggested that synthetic ST is a more effective immunogen than the B subunit. This led to selection of a cross-linked immunogen for evaluation by immunization in rats that contained roughly one-third ST and two-thirds B subunit antigenic activity. When given in large p.o. doses, that vaccine aroused at least a 4-fold serum and mucosal antitoxin response against both component toxins, thus providing significant protection against challenge by either the ST or LT toxins and heterologous viable bacteria which produce either toxin form.

Since all ETEC strains evoke diarrhea through the elaboration of the LT or ST toxins, either singly or together, the arousal of a sufficiently strong antitoxin response to each of these toxins provides uniformly effective protection against all ETEC strains irrespective of the somatic serotype, specific fimbrial antigen or type of toxin produced. Such was shown to be the case in the above study among rats immunized with the cross-linked ST-B subunit vaccine.

Immunization with LT given exclusively by the parenteral route aroused only a serum IgG antitoxin response which provided only transient protection in rats, whereas p.o. booster immunization yielded extended protection due to the arousal of mucosal secretory Ig antitoxin. [Klipstein et al., *Infect. Immun.*, 37:1086-1092 (1982) and Klipstein et al., Ibid., 27:81-86 (1982)].

Mucosal secretary IgA antitoxin titers to both ST and the B subunit in rats immunized perorally with the cross-linked vaccine in the above study exceeded those previously found necessary to provide extended protection in rats immunized with just LT. This makes it clear that the cross-linked vaccine should be given by the p.o. route. The above data are insufficient to determine whether primary immunization by the parenteral route is a prerequisite for subsequent effective p.o. immunization since such has been found to be the case for rats immuzined with LT [Klipstein et al., *Infect. Immun.*, 31:144–150 (1981); Ibid., 37:1086–1092 (1982); and Ibid., 27:81–86 (1980)] and rats and dogs immunized with cholera toxoid [Pierce et al., *Infect. Immun.*, 21:185–193 (1978); Pierce et al. *J. Infect. Dis.*, 135:888–896 (1977)].

Figure 9:
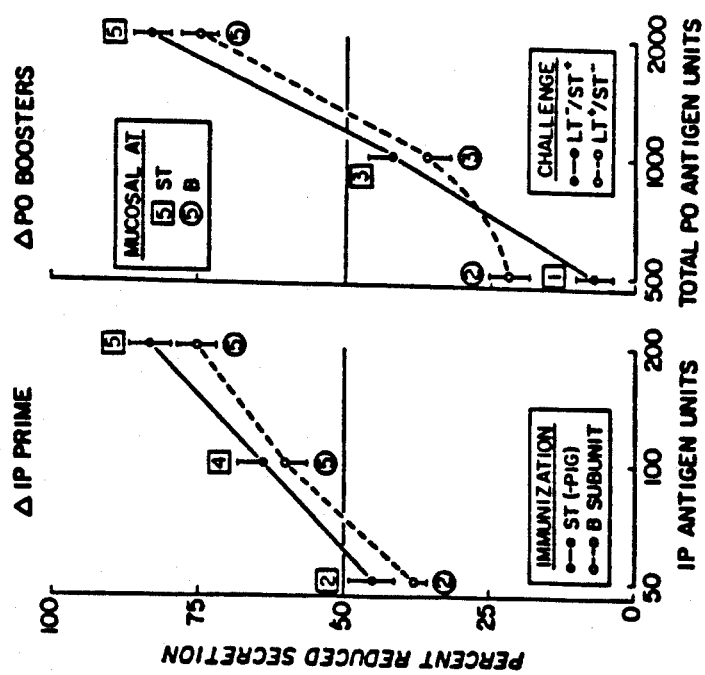

C. Synthetic ST Immunizations In Rats
Immunogenicity of ST and the B Subunit Rats were immuzined with graded antigen unit dosages of either the B subunit or synthetic ST coupled to porcine immunoglobulin G (PIG; Materials and Methods section C) as is shown in FIG. 9. Those rats given variable dosages of the i.p. primary immunization all received two p.o. booster immunizations of 1000 antigen units each, and those given variable dosages for the p.o. boosters all received i.p. primary immunization with 200 antigen units. Rats immunized with ST were challenged with human $LT^-/ST^+$ strain Tx 452 and those immunized with the B subunit were challenged with human $LT^+/ST^-$ strain PB 258.

Increasing the antigen unit dosages of either the i.p. primry immuniztion or the p.o. boosters of either immunogen resulted in parallel increases in antitoxin titers and in the degree of protection against challenge with the respective organisms. Values for serum IgG antitoxin titers rose proportionately but were consistently one or two-fold less than mucosal IgA antitoxin titers.

Dosages of either immunogen of 100 antigen units for i.p. primary immunization and a total of 2000 antigen units for the p.o. boosters (i.e., 2 boosters of 1000 antigen units each) were required to achieve at least 4-fold increases in mucosal IgA antitoxin titers and significant protection (i.e., greater than 50% reduced secretion) against challenge with the respective LT- or ST-producing strain.

Protection Against an $LT^-/ST^-$ Strain

Figure 10:
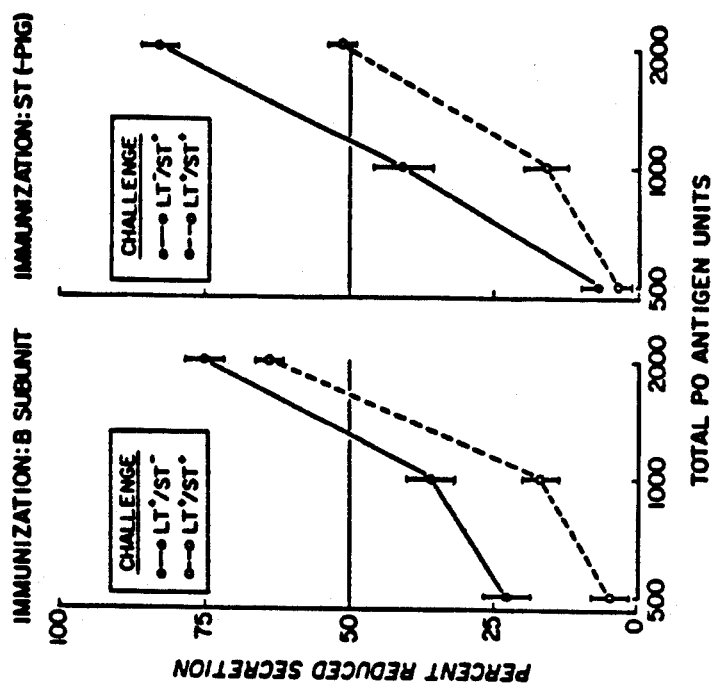

In order to determine the minimum antigen unit dosage of ST or B subunit necessary to achieve strong protection against a strain which produces both LT and ST, rats were immunized with each toxin separately, using an i.p. primary immunization of 200 antigen units followed by variable antigen unit dosages of the p.o. boosters, and were challenged both with the respective LT- or ST-producing strains and with human $LT^+/ST^+$ strain H 10407 (FIG. 10).

Strong protection against the $LT^-/ST^-$ strain was achieved only by a total p.o. booster dosage of 2000 antigen units. In each instance, the degree of protection against the $LT^-/ST^-$ strain was less than that for the strain which produced only the single homologous toxin.

Conjugation Conditions for the Vaccine

The preceding observations indicate that the optimal vaccine should contain equal antigenic proportions of each component toxin. It was shown in Section B, hereinabove, that when the ratio of carbodiimide to total conjugate protein is kept constant at 1.5:1 by weight, increasing the initial molar ratio of ST mixed with the B subunit yields a final conjugate with progressively more ST and less B subunit antigenicity.

Figure 11:
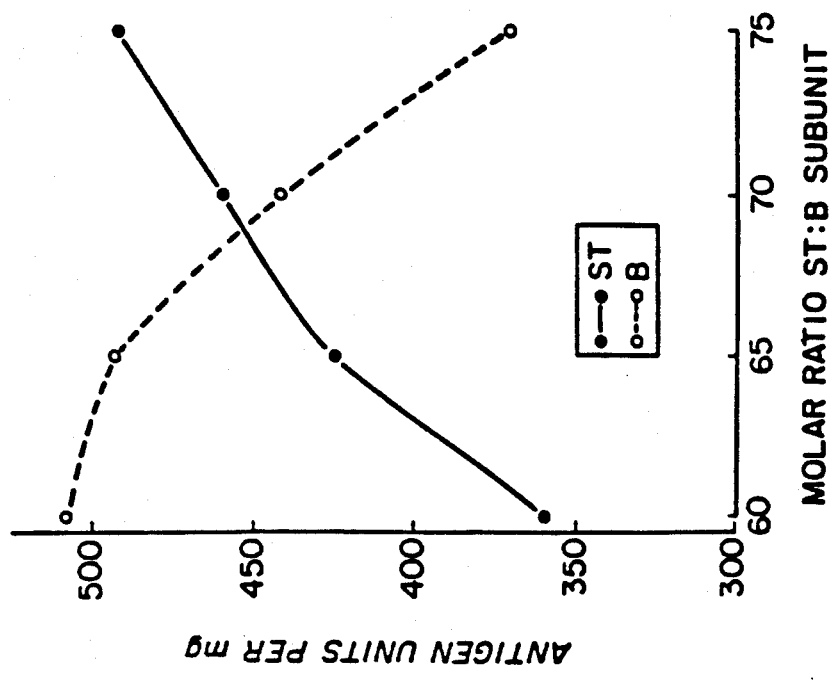

When the initial molar ratio of ST to B subunit was varied between about 60:1 to about 75:1, it was found that a ratio of about 70:1 resulted in a conjugate which consisted of 50% of each toxin component by weight and contained 460 ST and 440 B subunit antigen units per milligram (FIG. 11). All subsequent conjugates discussed in this section were prepared in this manner. In five consecutive lots, mean antigen units per milligram were 474 for ST and 460 for the B subunit using the above ratios.

Properties of the Vaccine (i) Immunogenicity

Figure 12:
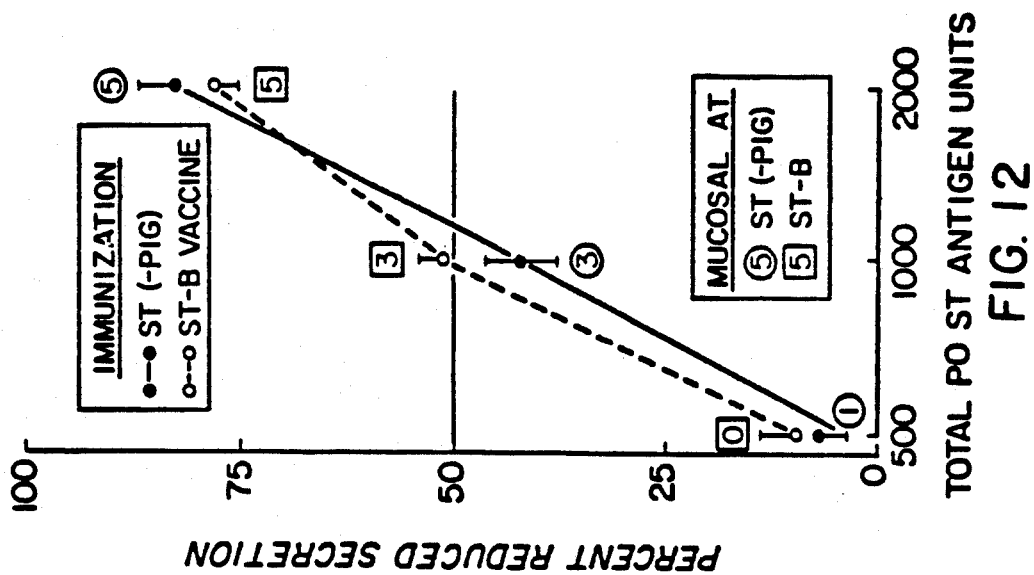

In order to confirm the fact that the immunogenicity of the toxin components cross-linked in vaccine form is the same as that of the individual components, rats were immunized by i.p. primary immunization of 200 ST antigen units followed by graded p.o. booster dosages of ST given either in vaccine form or coupled to the immunologically nonspecific carrier PIG. The results are shown in FIG. 12. As seen in FIG. 12, the antitoxin response and degree of protection against the human $LT^-/ST^+$ strain were substantially identical in rats immunized with either form of ST conjugate.

(ii) Toxicity

Figure 14:
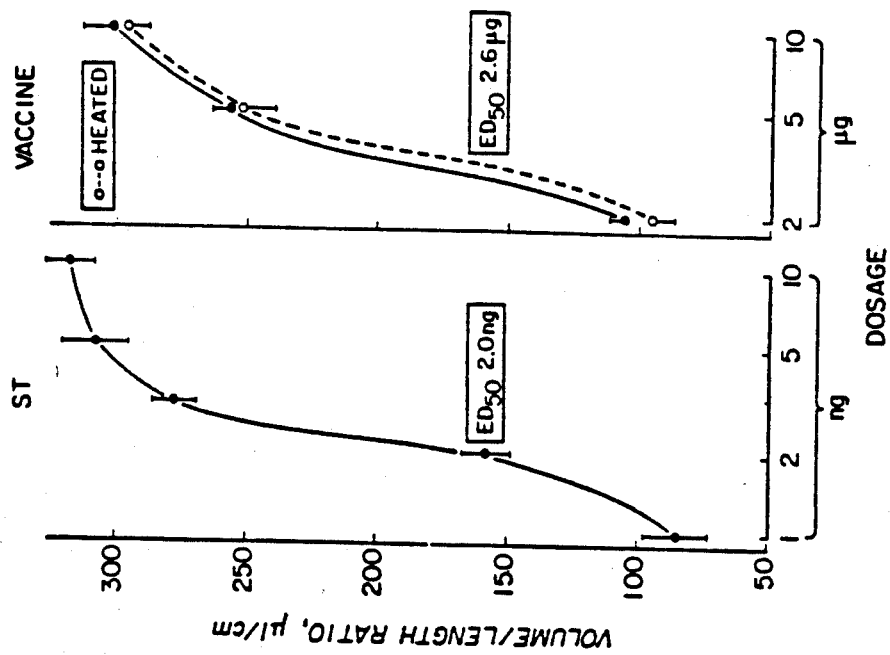
Figure 13:
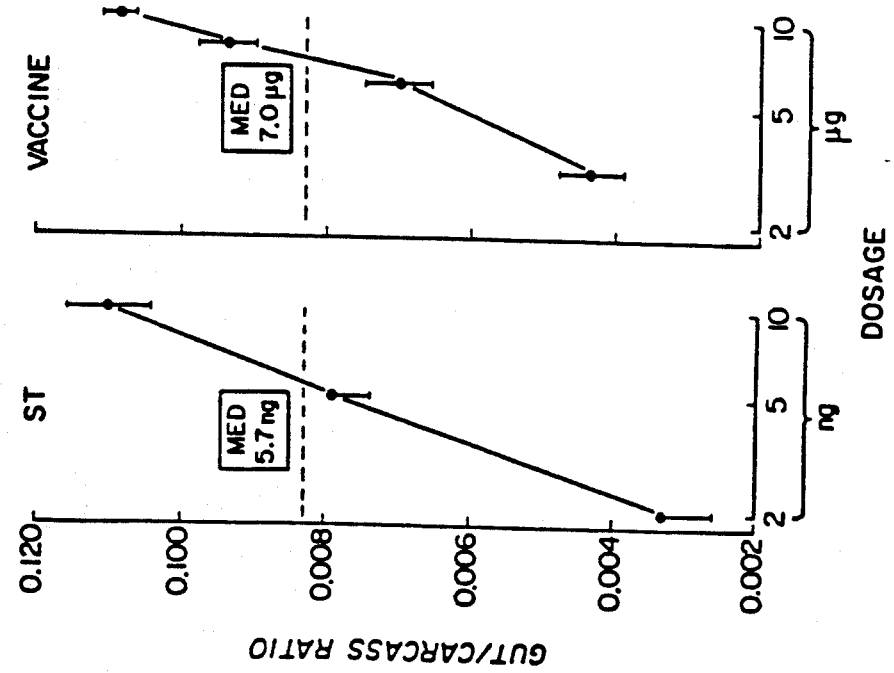

Assay of graded amounts (by protein content) of ST alone or of the vaccine in suckling mice showed that the vaccine contained 0.14 mouse units of ST activity per microgram, which represented 0.08% of the value of 175 mouse units per microgram of ST alone (FIG. 13). When graded amounts of either ST alone or the vaccine were tested in rat ligated ileal loops, the $ED_{50}$ of the vaccine, 2.6 micrograms was 0.08% that of the value of the 2.0 nonograms for ST alone (FIG. 14). The B subunit alone had an $ED_{50}$ of 95 nanograms in ligated ileal loops which was 0.2% of the value of 0.19 nanograms for the LT holotoxin. Whether this secretory activity was due to the B subunit itself or a manifestation of slight, otherwise undetected contamination with LT is uncertain.

In order to determine whether the B subunit component was contributing to the residual secretory activity of the vaccine in the rat ligated ileal loop assay, graded dosages of vaccine were tested after heat inactivation of the B subunit (or its LT contaminant) by exposure to 65° C. for 1 hour. The secretory response to heated and unheated vaccine was the same, excluding a role for the B subunit in this response. These observations indicate that the toxicity of a dosage of vaccine containing 1000 antigen units of each component toxin would consist of the equivalent of 1.7 micrograms of unattenuated ST.

(iii) Protection Against Human and Porcine Strains

Rats were immunized by primary i.p. immunization with vaccine containing 200 antigen units of each component toxin and two p.o. boosts, each of which had 1000 antigen units of each toxin component. This raised serum IgG antitoxin titers to both toxin components by 3-fold and mucosal IgA antitoxin titers by 5-fold to ST and by 6-fold to the B subunit. The immunized rats were significantly protected (P less than 0.001) against challenge with viable human or porcine strains which produce LT or ST toxin, either singly or together, as is shown in Table 5, below.

TABLE 5

Results of Challenge In Rats Immunized With the Cross-Linked Vaccine

| Source | Toxicity | Strain | Serotype | % Reduced Secretion |
|---|---|---|---|---|
| Human | LT−/ST− | PB 257 | 015:H− | 74 ± 1 |
| Porcine | LT−/ST− | P 263 | 08:H19 | 72 ± 3 |
| Human | LT−/ST− | H 10407 | 078:H11 | 61 ± 1 |
| Porcine | LT−/ST− | P 1362 | 0149:H?[b] | 73 ± 2 |
| Human | LT−/ST− | Tx 452 | 078:H12 | 79 ± 2 |
| Porcine | LT−/ST− | P 987 | 09:H− | 81 ± 2 |

Mean ± standard error of the mean percent reduced secretion in immunized rats as compared to similarly challenged unimmunized animals. Values of more than 50% represent a significant (P less than 0.001) difference between the two groups.
[b]The complete identification of this serotype is uncertain.

Primary parenteral immunization was given to an additional group of rats by the subcutaneous (s.c.) route using alum as the adjuvant, prepared as described previously for LT immunization [Klipstein et al., *Infect. Immun.*, 37:1086-1092 (1982)]. Since this approach has been found to require twice the dosage used for the i.p. route for effective LT primary immunization, the s.c. dosage of the vaccine given was doubled to 400 antigen units; the p.o. dosage was unchanged at 1000 antigen units. This raised at least a 5-fold mucosal IgA antitoxin titers to both toxin components and provided significant protection against challenge, with secretion reduced by 77±3% against the human LT+/ST− strain and by 71±2% against the human LT−/ST+ strain.

The above results indicate that, when evaluated in the manner of Klipstein et al., *Infect. Immun.*, 31:144-150 (1981), the immunogenicity of synthetically-produced ST is substantially the same as that of the B subunit. Essential to this comparison was the expression of dosage of conjugated toxin in terms of antigen units rather than on a weight basis.

This information led to modifying the conjugation conditions used previously to cross-link synthetic ST to the B subunit, Section B above, in order to produce a vaccine that contains equal antigenic proportion of ST and B subunit. The immunogenicity of the synthetic ST component in vaccine form was shown to be identical to that of this toxin when given coupled to a nonspecific immunoglobulin carrier. Immunization of rats with vaccine, given at those antigen unit dosages found effective for each of the component toxins given seprately, raised a strong antitoxin response to each of the component toxins and provided significant protection against viable ETEC strains that produce LT or ST, either singly or together. Observations derived from immunizations with each toxin component given separately indicated that the protection affored by the vaccine against the LT−/ST+ strain was attributable to both toxin components.

Frantz and Robertson have reported that antisera to porcine ST reacts with ST from ETEC strains of porcine, bovine, and human origin [*Infect. Immun.*, 33:193-198 (1981)]. The above results indicate that cross-protection can be achieved by immunization with either toxin irrespective of its source. Thus, immunization with the cross-linked vaccine containing a B subunit derived from porcine LT and synthetic ST based on the structure of human ST provided equally strong protection against human and porcine LT- and ST-producing strains.

Immunization was given in the above study by means of parenteral primary immunization followed by p.o. boosters because it was previously found in the rat animal model that, (1) parenteral priming is a prerequisite for strongly effective p.o. booster immunization, (2) only p.o. immunization raises mucosal IgA antitoxin titers, and (3) extended protection is achieved only when a sufficient p.o. dosage is given that raises mucosal IgA titers by at least 4-fold. Immunization with the cross-linked vaccine by this approach yielded increases of this magnitude in mucosal IgA antitoxin titers to both of the component toxins. The subcutaneous (s.c.) route and alum adjuvant were shown to be equally effective for immunization.

D. Synthetic ST Immunization in Rabbits

The above discussed results (Section C) were obtained in the rat using i.p. immunizations followed by p.o. boosters. The results discussed below were obtained in rabbits using the peroral route of administration for both the primary and booster immunizations.

The results below indicate that the peroral route of immunization is equally as effective as is the i.p. route. In addition, it is noted that the vaccine did not cause diarrhea in any animal when given by the p.o. route, nor did it cause fluid secretion when instilled into rabbit ligated ileal loops.

Rats (i) i.p./p.o. Immunization

Figure 15:
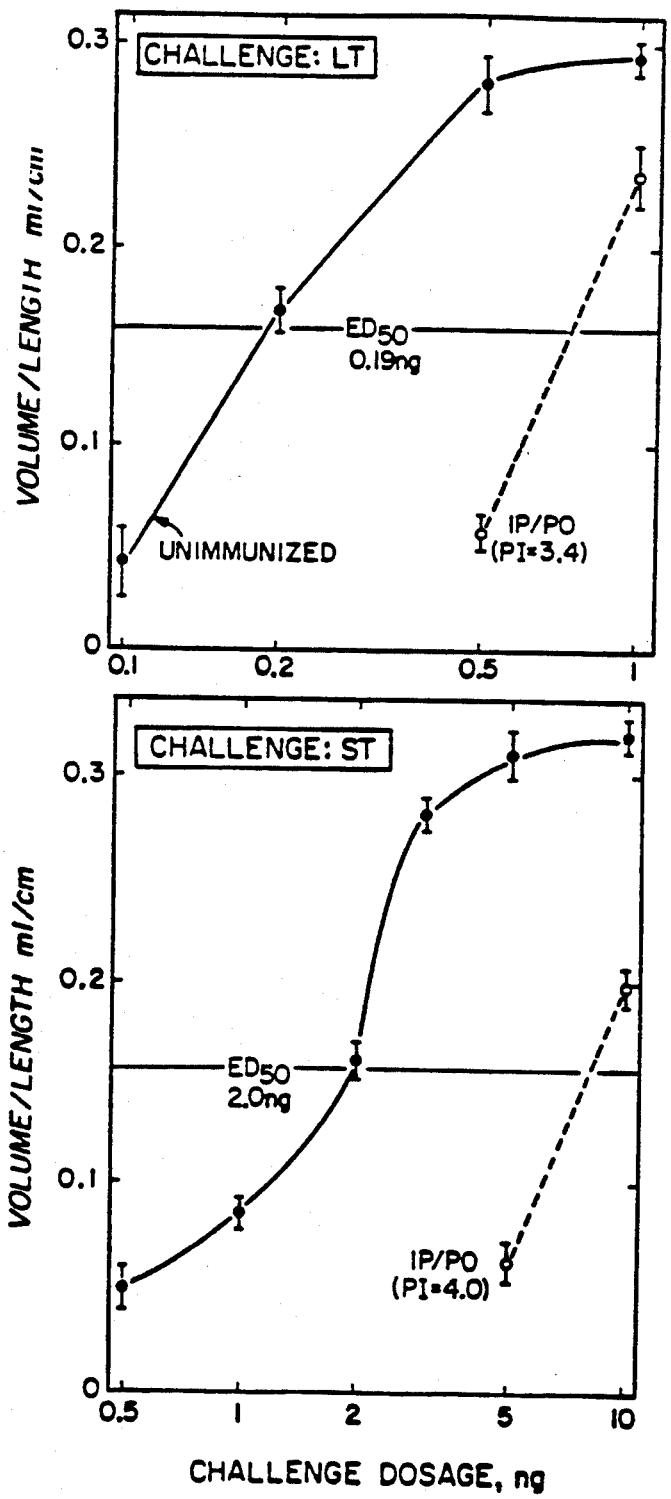

Rats received primary immunization with 200 AU (antigen units; see Materials and Methods Section D) of vaccine given i.p. with Freund's complete adjuvant (FCA) followed by two p.o. boosters of 1000 AU each. This dosage was selected because it has been shown (Section C, supra) to be the minimal amount necessary to provide significant (P less than 0.001) protection against challenge with viable strains which produce either toxin form. This immunization raised 4-fold increases in serum, and at least 6-fold increases in mucosal, antitoxin titers to each toxin component of the vaccine (Table 6, below) and it provided protection index (PI) values of 3.4 against challenge with LT and 4.0 against challenge with ST (FIG. 15).

TABLE 6

Antitoxin Response And Degree Of Protection in Immunized Animals

| Animal Model | Route of Immunization | Antitoxin to B[a] Serum | Antitoxin to B[a] Mucosal | Antitoxin to ST Serum | Antitoxin to ST Mucosal | Protection Index vs LT | Protection Index vs ST |
|---|---|---|---|---|---|---|---|
| Rats | i.p./p.o. | 4 | 6 | 4 | 7 | 3.4 | 4.0 |
| Rabbits | i.m.[b]/p.o. | 5 | 4 | 6 | 4 | 9.3 | 10.0 |
| Rabbits | p.o./p.o. | 3 | 5 | 2 | 4 | 8.6 | 8.1 |

[a]Values are the fold increase in the reciprocal of the geometric mean titer in immunized over control animals.
[b]i.m. = intramuscular.

(ii) Other Immunization Approaches

In order to determine the effectiveness of other parenteral routes, adjuvants and p.o. delivery systems, additional groups of four rats each were given primary immunization with 400 AU of vaccine by the subcutaneous (s.c.) route using alum as the adjuvant, prepared as described previously for LT [Klipstein et al., *Infect Immun.*, 37:1086-1092 (1982)]; this was followed by two p.o. boosters, each of 1000 AU, given either 2 hours after p.o. cimetidine or in the form of pH-dependent microspheres without pretreatment with cimetidine. When challenged with LT−/ST+ strain Tx 452, each of these alternative approaches to immunization yielded the same significant (P less than 0.001) degree of reduced secretion as that achieved by using the i.p. route with FCA followed by p.o. boosters given after cimetidine. These results are shown in Table 7, below.

TABLE 7

Effectiveness of Alternative Routes, Adjuvants And Delivery Systems Of The Vaccine in Rats

| Primary Route/Adjuvant | Booster Route/Protection | Protection vs LT−/ST+[a] |
|---|---|---|
| i.p./FCA | p.o./cimetidine | 79 ± 2 |
| s.c./alum | p.o./cimetidine | 71 ± 2 |
| s.c./alum | p.o./microspheres | 67 ± 2 |

[a]Mean ± SEM percent reduced secretion in immunized animals as compared to similarly challenged unimmunized controls. Values of more than 50% represent a significant (P less than 0.001) difference between the two groups.

Rabbits (i) i.m./p.o. Immunization

Figure 16:
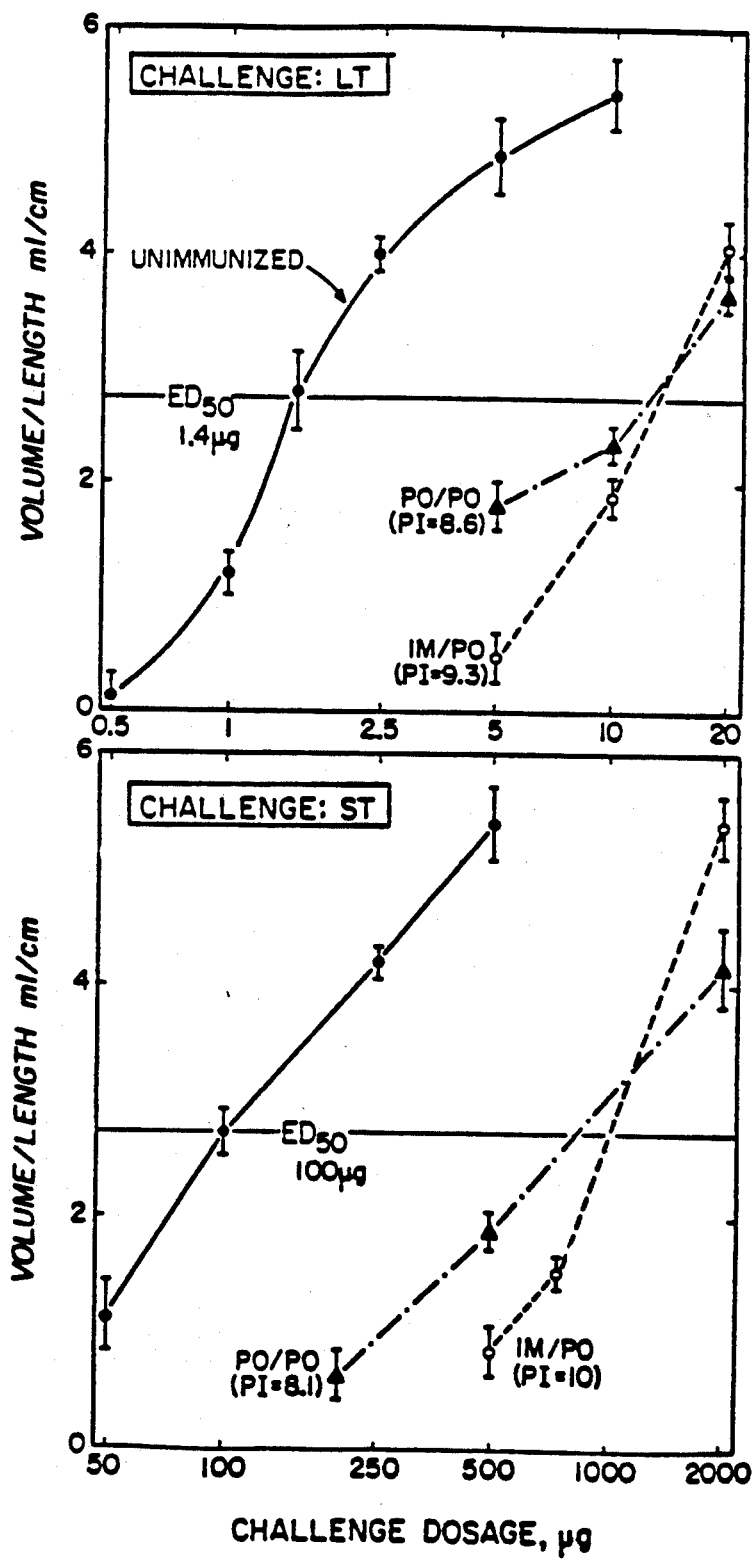

Four rabbits received primary immunization with 500 AU of vaccine given intramuscularly (i.m.) with FCA, followed by two p.o. boosters of 1000 AU each. This raised more than 5-fold increases in serum, and 4-fold increases in mucosal antitoxin titers to each component of the vaccine. PI values were more than 9 against challenge with either LT or ST. These data are shown in FIG. 16, and Table 6, supra.

(ii) p.o./p.o. Immunization

Four rabbits received immunization with 1000 AU of vaccine given p.o. on three occasions. This raised 4-fold increases in mucosal, but not in serum, antitoxin titers and provided strong protection, with PI values of more than 8 against challenge with either toxin form. These data are also shown in Table 6, supra.

Toxicity of the Vaccine

Previous studies (Section C) have shown that the toxicity of the ST component of the vaccine is reduced to 0.15% of unattenuated toxin. A dosage of 1000 AU of vaccine would thus contain the equivalent of 1.7 micrograms of unattenuated ST (0.15% times the 50% ST component of 2.2 milligrams). The toxicity of this dosage of the vaccine and of larger amounts of unattenuated ST was evaluated in unimmunized animals. (i) The p.o. administration of 1000 AU of vaccine to eight rabbits and 20 rats produced no adverse effects such as diarrhea, and the instillation of this dosage of vaccine into four ligated ileal loops in two rabbits failed to evoke any fluid response. (ii) The p.o. administration of 250 micrograms of unattenuated ST to two rabbits and rats did not cause diarrhea. The instillation of 25 micrograms of unattenuated ST did not cause any fluid secretion in ligated ileal loops of four rabbits; a dosage of 50 micrograms was required to yield a positive fluid:length ratio of 1.1±0.3 (mean ± SEM).

The results of the above study establish the effectiveness of immunization with a vaccine made using a synthetic ST of this invention in an experimental animal model, rabbits, in addition to rats. Protection in both animal models was demonstrated by use of the ligated ileal loop technique. The applicability of this technique to protection under conditions in which the entire intact intestine is acutely colonized by enterotoxigenic strains of *E. coli* has been confirmed in rats immunized with LT [Klipstein et al., *Infect. Immun.*, 28:163-170 (1980)].

The same p.o. dosage of vaccine (1000 AU), given after primary parenteral immunization, resulted in a considerably stronger degree of protection, as manifested by PI values, in rabbits than in rats. This difference may in part be attributable to the longer interval between immunizations used for rabbits (14 days versus four days in rats), and perhaps to differences in sensitivity to toxin challenge. It also probably indicates that rabbits are more responsive to immunization with the vaccine than rats. This dosage used was the minimum found required to achieve significant protection against viable enterotoxigenic strains in rats (Section C, supra).

The fact that this dosage was also effective in providing strong protection in a larger experimental animal points to utility in animal husbandry and humans. This is also suggested by the observations of Svennerholm et al. who found that a p.o. immunization dosage of 500 micrograms of cholera toxin B subunit is sufficient to arouse a significant intestinal IgA antitoxin response in human volunteers [*Lancet*, 1:305-308 (1982)].

The results of the present study indicate that exclusive p.o. immunization of rabbits with the synthetic ST-B vaccine achieved the same strong degree of protection as that achieved by p.o. booster immunizations following parenteral primary immunization.

IV. Materials and Methods

A. Enterotoxin Production

The complete procedure for synthesis and purification of the synthetic ST used herein and in each following lettered section is described in detail in Section II.

Biologic ST was purified to homogeneity from culture filtrates of strain 18D by a modification [Klipstein et al. *Infect. Immun.*, 37:550–557 (1982)] of the methods described by Staples et al., supra. The amounts of toxins were based on their protein concentration determined by the method of Lowry et al., *J. Biol. Chem.*, 193:265–275 (1951).

Assay of Secretory Potency

The ability of graded dosages of the toxins to cause secretion was tested in the suckling mouse and rat ligated ileal loop assays using published methods [Giannella, *Infect. Immun.*, 14:95–99 (1976) and Klipstein et al., Ibid., 34:637–639 (1981)]. One mouse unit (MU) in the suckling mouse assay is defined as that amount of toxin which yields an intestinal (gut):carcass weight ratio of at least 0.083.

Production of Hyperimmune Antiserum

Hyperimmune antiserum was raised in goats and rabbits to biologic ST as described previously [Klipstein et al., *Infect. Immun.*, 37:550–557 (1982)]. Synthetic ST was coupled to porcine immunoglobulin G (PIG) by mixing ST to PIG at a molar ratio of 100:1, using a ratio by weight of 1-ethyl-3-(3-dimethylaminopropyl) carbodiimide to total conjugate protein of 2:1, in 0.1 molar phosphate buffer, pH 7.0, for 18 hours, at 4° C. This conjugate contained 47% ST by weight and 98% ST by moles. The conjugated ST retained 73% of its antigenicity, determined by enzyme-linked immunosorbent assay (ELISA) using hyperimmune goat and rabbit antisera to biologic ST in a previously described double sandwich technique (Ibid.). The conjugate thus contained 343 antigen units (derived by multiplying the percentage of ST present by weight times the percentage of its antigenicity) per milligram of protein. Animals were immunized intramuscularly with Freund complete adjuvant (FCA) for the primary immunization and Freund incomplete adjuvant for the booster immunization given one month later. Goats received 1,100 followed by 2,300 ST antigen units, and rabbits received 300 followed by 500 ST antigen units.

Immunization and Challenge of Rats

Weanling Sprague-Dawley rats were immunized with the synthetic ST-PIG conjugate by means of an intraperitoneal primary immunization of 350 ST antigen units given with Freund complete adjuvant followed at 4 day intervals by two peroral booster immunizations containing 700 ST antigen units each, which were given 2 hours after the peroral administration of cimetidine in order to ablate gastric acidity. They were challenged 5 days after the final boost by the instillation for 18 hours into a single ligated ileal loop of concentrations which evoke maximum secretion in unimmunized rats: 5 nanograms of either synthetic or biologic ST and 0.1 milliliter of a broth culture containing $10^9$ viable organisms per milliliter of ST-producing human *E. coli* strain Tx 452 (078:H12). Five unimmunized and three immunized rats were challenged with each test material. Values are expressed as the means ± standard error of the mean percent reduced secretion in immunized rats as compared to that in unimmunized controls; in each instance more than 50% reduced secretion represents a significant difference (P less than 0.001) between the two groups as determined by Student's t-test for two independent means.

Antitoxin response to immunization

At the time of challenge, serum and mucosal washings were processed as described previously [Klipstein et al., *Infect. Immun.*, 37:1086–1092 (1982)] and assayed by a double sandwich ELISA in which goat hyperimmune antiserum to synthetic ST was used for the solid phase and synthetic ST was employed as the antigen. Klipstein et al. found that in rats similarly immunized with LT, only serum antitoxin of the immunoglobulin G (IgG) and mucosal antitoxin of the immunoglobulin A (IgA) class can be detected (Ibid.); therefore, antitoxin to synthetic ST was evaluated for only these two immunoglobulin classes using rabbit anti-rat IgG together with goat anti-rabbit antiserum conjugated to alkaline phosphatase for serum samples and goat anti-rat secretory IgA together with rabbit anti-goat antiserum conjugated to alkaline phosphatase (Miles Research Laboratories, Elkhart, Indiana) for mucosal samples. Values reported are for the geometric mean titer in 9 immunized and 5 unimmunized control rats.

Section B

Enterotoxin preparations

Purified LT holotoxin was prepared by the methods described by Clements and Finkelstein, *Infect. Immun.*, 24:760–769 (1979) from *E. coli* strain 711 (FILT), a transformed K-12 derivative bearing LT gene(s) of the Ent plasmid from porcine strain P307. The B subunit was separated from the LT holotoxin by the chromatogrphic techniques described by Clements et al., Ibid., 29:91–97 (1980). The homogeneity of the LT toxin and its B subunit was confirmed by polyacrylamide gel electrophoresis as described by Clements and Finkelstein, supra.

Biologic ST, obtained by growth of human *E. coli* strain 18D (042:H47), was purified by the methods described by Staples et al, supra, with the modification that final purification to homogeneity was achieved by elution from thin layer chromatography as described by Klipstein et al., Ibid., 37:550–557 (1982). Synthetic ST, consisting of the same sequence of 18 amino acids described by Chan et al., supra, for pure ST obtained by growth of strain 18D, was prpeared using a Beckman model 990 B peptide synthesizer (Beckman Instrument Co., Irvine, Calif.) by methods reported in Section II. The synthetic toxin was shown to be substantially identical to that obtained by culture techniques (biologic ST) in terms of secretory potency in the suckling mouse assay and antigenicity as determined by enzyme-linked immunoadsorbent assay (ELISA) and by seroneutralization of secretory activity in the suckling mouse assay by hyperimmune antiserum to either the synthetic or biologic toxin in Section III, hereinbefore.

The amount of toxins used, stated as weight, was based on protein concentrations determined by the method of Lowry et al., supra. Molar equivalents were derived from published values of a molecular weight of 91,450 daltons for LT by Clements et al., supra, 57,400 for the polymeric 5 B subunits by Gill et al., *Infect. Immun.*, 33:677–682 (1981), and 1,972 daltons for ST by Staples, et al., supra.

Radioiodination of ST

Synthetic ST was radioiodinated by the chloramine-T method of Hunter, *Proc. oc. Exp. Biol. Med.*, 133:989–992 (1970) using procedures described previously for pure biologic ST by Klipstein et al., *Infect Immun.*, 37:550–557 (1982). The radiolabelled toxin contained 3×10⁵ counts per minute and 71 mouse units per microgram (versus 175 mouse units per microgram for unlabelled toxin) as determined by the suckling mouse assay in which one mouse unit is defined as that amount which yields an intestinal weight:carcass weight ratio of at least 0.083.

Conjugation

ST was conjugated either to LT or to the B subunit by adding 1-ethyl-3-(3-dimethylaminopropyl) carbodiimide (EDAC) (Sigma Chemical Co., St. Louis, Mo.) to mixtures of the toxins in 0.1 molar phosphate buffer at a pH 7.0 for 18 hours at 4° C. The conjugate was then exhaustively dialysed against water for 48 hours at 4° C. using a 12,000 molecular weight cutoff dialysis bag which retained all of the LT (or B subunit) and conjugated ST but not unconjugated ST or EDAC. Repeated determinations showed that dialysis against water of either LT or the B subunit alone resulted in a 10% loss due to precipitation. Therefore, the amount of ST conjugated was based on the incremental increase in Lowry protein present in the dialysand that was in excess of 90% of the amount of either LT or B subunit initially added. The amount of radioiodinated ST conjugated was ascertained by comparing the radioactivity of the final conjugates to that initially added using an autogamma counter sold under the trademark PRIAS PGD by Packard Instrument Co., Downers Grove, Ill.

Properties of the Conjugate

Unless otherwise specified, the concentration of each conjugate was adjusted to represent 100% of the specific toxin tested in studies which compared the properties of conjugated toxins to those of unattenuated toxin. LT toxicity was compared by assaying serial 2-fold dilutions of LT alone and in conjugated form in the Y1 adrenal cell assay of Sack et al., *Infect. Immun.*, 11:334–336 (1975). ST toxicity was compared by establishing the minimal effective dosage of serial dilutions of synthetic ST alone or in conjugated form in the suckling mouse assay of Klipstein et al., *Ibid.*, 37:550–557 (1982).

Antigenicity was determined by means of ELISA. Monospecific goat hyperimmune antiserum to either LT or the B subunit of cholera (Clements et al., supra) were used with rabbit anti-goat antiserum conjugated to alkaline phosphatase (Miles Research Laboratories, Elkhart, Ind.). For ST, hyperimmune antiserum to pure biologic ST raised in goats and rabbits as described previously [Klipstein et al., *Infect. Immun.*, 37:550–557 (1982)] was used in a double sandwich technique along with rabbit anti-goat antiserum conjugated to alkaline phosphatase; values for the conjugates were compared to that of synthetic ST in this assay. Starting at 10 micrograms, serial 2-fold dilutions were made of the conjugates and appropriate toxin. That concentration at which these preparations yielded an adsorbance of 0.600 at 410 nanometers was used to compare the antigenicity of the toxin in conjugated and unattenuated form.

Immunization Procedures

Rats were given primary immunization intraperitoneally (i.p.) using Freund complete adjuvant followed by two peroral (p.o.) boosters at 4 day intervals. Peroral immunization was given via an intragastric tube 2 hours after the p.o. administration of cimetidine (sold under the trademark TAGAMET by Smith, Kline and French Laboratories, Carolina, Puerto Rico), at a dosage of 50 milligrams/kilogram of body weight in order to ablate gastric secretion.

Challenge Procedures

Rats were challenged 1 week after the final boost by the instillation of test material into a single 10-centimeter ligated loop of distal ileum for 18 hours as described previously [Klipstein et al., *Ibid.*, 31:144–150 (1981) and 32:1100–1104 (1981)]. Previous studies have established a correlation between significant protection in this assay system and that achieved in immunized rats challenged by intestinal contamination of the intact intestine [*Ibid.*, 28:163–170 (1980)]. Challenge dosages were those which evoked maximum secretion in unimmunized animals: 0.5 nanograms LT, 5 nanograms of either synthetic or biologic ST, and 0.1 milliliter of broth cultures containing 10⁹ viable organisms per milliliter of $LT^+/ST^-$ strain PB-258 (015:H⁻), $LT^-/ST^-$ strain H-10407 (078:H11), and $LT^-/ST^-$ strain Tx 452 (078:H12). Each datum point was determined in from 3 to 5 immunized rats and the values reported are the mean ± standard error of the mean (SEM) degree of reduced secretion in immunized rats as compared with the value in 5 similarly challenged unimmunized rats. Reduced secretion of 50% was significant for each challenge material at a P value of less than 0.001 as determined by Student's t-test for two independent means.

Antitoxin Response

Serum and musosal antitoxin titers to the synthetic ST and B subunit components of the vaccine were determined in the serum and mucosal washings of immunized rats by ELISA using techniques described in previous studies which showed that the antitoxin response of rats immunized with LT by the parenteral/peroral approach is confined to that associated with serum IgG and musocal IgA [*Ibid.*, 37:1086–1092 (1982)]. For this reason, only antitoxins of these immunoglobulin classes were assayed in the present study. For antitoxin to the B subunit, the B subunit was used as the solid phase; for antitoxin to synthetic ST, hyperimmune antiserum to synthetic ST developed in a goat was used as the solid phase and synthetic ST was used as the antigen in a double sandwich technique. For serum samples, rabbit anti-rat IgG and goat anti-rabbit antiserum conjugated to alkaline phosphatase were added; for mucosal washings, goat anti-rat secretory IgA and rabbit anti-goat antiserum conjugated to alkaline phosphatase (Miles Research Laboratories, Elkhart, Inc.) were used. The values reported are for the increase in the reciprocal of the geometric mean titer in samples from 5 immunized over those in 5 unimmunized control rats. Antitoxin titers in control animals were 1:2 against either ST or B subunit in all samples except that the serum titer against ST was 1:4.

Section C

Preparation of the Vaccine

Purified LT holotoxin was prepared from *E. coli* strain 711 (FILT), a transformed K-12 derivative bearing LT gene(s) of the Ent plasmid from porcine strain P307, and separated into its subunits by chromotographic techniques as discussed above, in Section B. The homogeneity of the LT holotoxin and its B subunit was confirmed by polyacrylamide gel electrophoresis as also discussed in Section B. Synthetic ST, consisting of the same primary structure of 18 amino acids described by Chan et al., supra, for pure ST obtained by purification of cultures of strain 18D, was prepared as per Section II, supra.

The amount of toxins used was based on their protein concentrations determined by the method of Lowry et al., supra; their molar equivalents were derived from published values of a molecular weight of 57,400 daltons for the polymeric form of five B subunits and 1,972 daltons for ST, as discussed in Section B, above.

ST was conjugated to the B subunit by adding 1-ethyl-3-(3-dimethylaminopropyl) carbodiimide (Sigma Chemical Co., St. Louis, Mo.) at a ratio by weight of 1.5:1 to the total protein of mixtures of varying molar ratios of the toxins in 0.1 M phosphate buffer at pH 7.0 for 18 hours at 4° C.; the conjugate was then exhaustively dialyzed against water and processed thereafter as described previously in Section B, above.

Properties of the Vaccine

The antigenicity of the component toxins in the vaccine was determined by means of enzyme-linked immunosorbent assay (ELISA) as described above in Section B. For the B subunit, monospecific goat hyperimmune antiserum to the B subunit of human LT was used with rabbit anti-goat antiserum conjugated to alkaline phosphatase (Miles Research Laboratories, Elkhart, Ind.). For ST, hyperimmune antiserum to synthetic ST raised in goats and rabbits (Section IV, A, above) was used in a double sandwith technique along with rabbit anti-goat antiserum conjugated to alkaline phosphatase. Starting at 10 micrograms, serial 2-fold dilutions were made of the conjugates and the appropriate toxin. The concentrations at which the conjugate and toxin yielded an adsorbance of 0.600 at 410 nanometers were compared and the value for the conjugate was expressed as a percentage of that of the unattenuated toxin. The percentage antigenicity times 1000 yielded the value for antigen units per milligram in the vaccine.

Residual toxicity in the vaccine was determined by comparing the values for ST and the vaccine of (i) the minimal effective dosage in the suckling mouse assay in which one mouse unit is defined as that amount which yields an intestinal weight/carcass weight ratio of at least 0.083, and (ii) the $ED_{50}$ (that dosage which yields one-half maximum secretion) in ligated ileal loops of unimmunized rats.

ST Conjugation

In those instances where rats were immunized with synthetic ST alone, the toxin was coupled to porcine immunoglobulin G (PIG) at a molar ratio of toxin to PIG of 100:1 and a carbodiimide to total conjugate protein ratio of 1:1 by weight. This conjugate contained 46% ST by weight and had 470 ST antigen units per milligram.

Immunization Procedures

Unless specified otherwise, rats were given primary immunization intraperitoneally (i.p.) using Freund complete adjuvant followed by two peroral (p.o.) boosters at 4 day intervals. Peroral immunization was given via an intragastric tube 2 hours after the p.o. administration of cimetidine (sold under the trademark TAGAMET by Smith, Kline and French Laboratories, Carolina, Puerto Rico), at a dosage of 50 milligrams/kilogram body weight in order to ablate gastric secretion.

Challenge Procedures

Rats were challenged 4 to 6 days after the final boost by the instillation into a single 10-centimeter ligated loop of distal ileum for 18 hours of 0.1 milliliters of broth cultures containing $10^9$ viable organisms per milliliter. Each datum point was determined in 3 to 5 immunized rats and the values reported are for the mean ± standard error of the mean of the degree of reduced secretion in immunized rats as compared with 5 unimmunized rats challenged with the same organisms. Reduced secretion of more than 50% is referred to as strong protection since it was significant in each instance at a P value of less than 0.001 as determined by Student's t-test for two independent means.

Antitoxin Response

Serum and mucosal antitoxin titers were determined by ELISA by techniques described in Section B, above. For antitoxin to the B subunit, the B subunit was used as the solid phase; for antitoxin to ST, goat hyperimmune antiserum to synthetic ST was used as the solid phase and synthetic ST was used as the antigen in a double sandwich technique. Since previous studies have shown that immunization with LT given by the i.p./p.o. approach arouses only serum IgG and mucosal IgA antitoxin titers [Klipstein et al., *Infect. Immun.*, 37:1086–1092 (1982)], only antitoxin of these immunoglobulin classes was evaluated. For serum samples, rabbit anti-rat IgG and goat anti-rabbit antiserum conjugated to alkaline phosphatase were added; for mucosal washings, goat anti-rat secretory IgA and rabbit anti-goat antiserum conjugated to alkaline phosphatase (Miles Research Laboratories, Elkhart, Ind.) were used. The values reported are for the increase in the reciprocal of the geometric mean titer in 5 immunized over that in 5 unimmunized control rats.

Section D

Preparation of the Vaccine

Purified LT holotoxin was prepared from *E. coli* strain 711 (F1LT), a transformed K-12 derivative bearing LT gene(s) of the Ent plasmid from porcine strain P307, and separated into its subunits by chromatographic techniques as discussed in Section B, above. The homogeneity of the LT holotoxin and its B subunit was also confirmed by polyacrylamide gel electrophoresis as discussed in Section B. Synthetic ST, consisting of the same primary structure of 18 amino acids as the polypeptide described by Chan et al., supra, and contained three intramolecular cystine disulfide bonds. The synthetic ST was that material whose specific preparation was given in Section II, above. The conjugation procedure used was the same as that discussed in Section III C, above, with the exception that the molar ratio of synthetic ST to B subunit was 70:1.

Properties of the Vaccine

Vaccine properties were determined as discussed in Section III C. The concentrations at which the vaccine and unattenuated ST and B subunit yielded an absorbance of 0.600 at 410 nanometers were compared and the value for each component of the vaccine was expressed as a percentage of that of the same toxin in unattenuated form. The percentage antigenicity times 1000 yielded the value for antigen units (AU) per mg in the vaccine. The vaccine used contained 450 AU of each component toxin per milligram of protein, and immunization dosages described as 1000 AU contained this amount of antigenicity for each toxin component in 2.2 milligrams of vaccine.

Immunization procedures

Unless specified otherwise, rats were given primary immunization intraperitoneally (i.p.) using Freund complete adjuvant (FCA) followed four days later by two p.o. boosters given at four day intervals. Peroral immunization was given via an intragastric tube 2 hours after the p.o. administration of cimetidine (sold under the trademark TAGAMET by Smith, Kline and French Laboratories, Carolina, Puerto Rico), at a dosage of 50 milligrams/kilogram body weight, in order to ablate gastric secretion. When given p.o. in microsphere form, 1000 AU of the vaccine was encapsulated by known techniques using hydroxypropyl methylcellulose phthalate (Compound HP-50, Sinetsu Chemical, Tokyo, Japan) as the pH-sensitive coating.

Rabbits were given primary immunization either by the intramuscular (i.m.) route using FCA or by the p.o. route using an intragastric tube; this was followed two weeks later by two p.o. boosters given at two week intervals. All p.o. immunizations were preceeded 2 hours before by an i.m. injection of 30 milligrams of cimetidine.

Antitoxin Response

At the time of challenge, serum and mucosal washings from challenge loops were processed [Klipstein et al., *Infect. Immun.*, 37:1086–1092 (1982)] and antitoxin titers were determined by ELISA using reported techniques discussed in Section B, above. For antitoxin to the B subunit, the B subunit was used as the solid phase; for antitoxin to ST, goat hyperimmune antiserum to synthetic ST was used as the solid phase and synthetic ST was used as the antigen in a double sandwich technique. Since previous studies, using LT as the immunogen, have shown that immunization by the i.p./p.o. approach arouses only serum immunoglobulin G(IgG) and mucosal IgA antitoxin titers (Klipstein et al., Ibid.), only antitoxin of these immunoglobulin classes were evaluated. The values reported are for the increase in the reciprocal of the geometric mean titer in four or more immunized animals over that in five unimmunized control animals, except for rabbit sera where pre- and post-immunication samples from the same animal were compared.

Challenge Procedures

Immunized animals were challenged four to seven days after the final booster immunization by the instillation of graded dosages of either ST or LT into ligated ileal loops for 18 hours as described previously Klipstein et al., *Infect. Immun.*, 31:144–150 (1981); Sack, Ibid., 8:641–648 (1973)]. The toxin was instilled in 0.5 milliliters of normal saline into a single loop in each rat and in 1.0 milliliters of Trypticase soy broth (BBL Microbiology Systems, Cockeysville, MD) in up to 10 loops in each rabbit. The values presented for each datum point of fluid secretion are the mean ± standard error of the mean (SEM) in from three to five control and immunized rats and in loops in six control rabbits and four rabbits in each immunization group. The protection index (PI) was determined by dividing that dosage of toxin in immunized animals which yielded the same secretion as the 50% effective dose (ED$_{50}$) in unimmunized animals by the value for unimmunized animals.

Rats were also challenged with 0.1 milliliter of a broth culture contrining 10$^9$ viable organisms of LT$^-$/ST$^+$ strain Tx 452 (078:H12) per milliliter. The results are expressed as the mean ± SEM percentage reduced secretion in immunized rats as compared to the value in five similarly challenged unimmunized control animals. The statistical difference between secretion in the immunized and control groups was determined by Student's t-test for two independent means.

What is claimed is:

1. A synthetic polypeptide, taken from left to right and in the direction from amino-terminus to carboxy-terminus, represented by the formula:

$$\text{Asn(Ser)Thr(Ser)Phe(Asn)TyrCys}(R_g^7)\overset{\overset{R_a^1}{|}}{\text{C}}\text{ys}(R_h^8)\overset{\overset{R_b^2}{|}}{\text{C}}\text{ys}(R_h^8)\text{Glu}$$

$$\text{LeuCyS}(R_i^9)\overset{\overset{R_c^3}{|}}{\text{C}}\text{ys}(R_j^{10})\overset{\overset{R_d^4}{|}}{\text{Tyr(Asn)ProAlaCys}}(R_k^{11})\overset{\overset{R_e^5}{|}}{\text{Ala(Thr)}}$$

$$\text{GlyCys}(R_l^{12})\overset{\overset{R_f^6}{|}}{\text{Asn(Tyr)}}$$

wherein $R_a^1$, $R_b^2$, $R_c^3$, $R_d^4$, $R_e^5$ and $R_f^6$ are the same or different moieties bonded to the sulfur atom of the Cys respective residue;

a-f are integers having a value of zero or one with the provisos that:

(I) "e" is zero when "a" is zero, "d" is zero when "b" is zero, and "f" is zero when "c" is zero;

(II) at least one of "a", "b" or "c" is zero whereby the corresponding $R_{a-c}^{1-3}$ is absent as is the $R_{d-f}^{4-6}$ whose subscript is zero when said "a", "b" or "c" is zero and an intramolecular disulfide bond is present between the respective Cys residues of said formula for which a subscript value of zero under proviso (I) requires another subscript value to be zero; and (III) when a value of a-f is one, said respective $R_{a-f}^{1-6}$ groups taken individually are selected from group consisting of hydrogen, an alkyl group containing 1 to about 4 carbon atoms, and a substituted alkyl group containing 2 to about 20 carbon atoms;

$R_g^7$, $R_h^8$, $R_i^9$, $R_j^{10}$, $R_k^{11}$ and $R_l^{12}$ are alternative Ser residues to the immediately preceding Cys residue shown in said formula;

g-l are integers having the value of zero or one whereby when the value of any g-l is zero the corresponding $R_{g-l}^{7-12}$-group is absent with the proviso that:

(IV) each of "g" and "k" is zero when "a" is zero, each of "h" and "j" is zero when "b" is zero, and each of "i" and "l" is zero when "c" is zero; and when the value of any of g-l is one, said corresponding $R_{g-l}^{7-12}$-groups are present;

said synthetic polypeptide having at least about 10% of the antigenicity of that of biologic heat stable enterotoxin of *Escherichia coli* and having thin layer chromatographic and electrophoretic mobilities different from said biologic heat stable enterotoxin.

2. The synthetic polypeptide according to claim 1 wherein g-l are zero and said polypeptide is substantially free of sulfhydryl groups.

3. The synthetic polypeptide according to claim 2 wherein the values of "b" and "d" are zero, the values of "a", "c", "e" and "f" are one, and $R_a{}^1$, $R_c{}^3$, $R_e{}^5$ and $R_f{}^6$ are carboxymethyl.

4. The synthetic polypeptide according to claim 2 wherein the values of "b", "c", "d" and "f" are zero, the values of "a" and "e" are one, and $R_a{}^1$ and $R_f{}^5$ are carboxymethyl.

5. A synthetic polypeptide, taken from left to right and in the direction from amino-terminus to carboxy-terminus, represented by the formula:

AsnThrPhe
TyrCys($R_g{}^7$)Cys($R_h{}^8$)GluLeuCys($R_i{}^9$)Cys($R_j{}^{10}$)
TyrProAlaCys($R_k{}^{11}$)AlaGlyCys($R_l{}^{12}$)Asn wherein
$R_a{}^1$, $R_b{}^2$, $R_c{}^3$, $R_d{}^4$, $R_e{}^5$ and $R_f{}^6$ are the same or different moieties bonded to the sulfur atom of the Cys respective residue;
a-f are integers having a value of zero or one with the provisos that:
(I) "e" is zero when "a" is zero, "d" is zero when "b" is zero, and "f" is zero when "c" is zero;
(II) at least one of "a", "b" or "c" is zero whereby the corresponding $R_{a-c}{}^{1-3}$ is absent as is the $R_{d-f}{}^{4-6}$ whose subscript is zero when said "a", "b" or "c" is zero and an intramolecular disulfide bond is present between the respective Cys residues of said formula for which a subscript value of zero under proviso (I) requires another subscript value to be zero; and
(III) when a value of a-f is one, said respective $R_{a-f}{}^{1-6}$ groups taken individually are selected from group consisting of hydrogen, carboxymethyl and carboxyamidomethyl;
$R_g{}^7$, $R_h{}^8$, $R_i{}^9$, $R_j{}^{10}$, $R_k{}^{11}$ and $R_l{}^{12}$ are alternative Ser residues to the immediately preceding Cys residue shown in said formula;
g-l are integers having the value of zero or one whereby when the value of any g-l is zero the corresponding $R_{g-l}{}^{7-12}$-group is absent with the proviso that:
(IV) each of "g" and "k" is zero when "a" is zero, each of "h" and "j" is zero when "b" is zero, and each of "i" and "l" is zero when "c" is zero; and when the value of any of g-l is one, said corresponding $R_{g-l}{}^{7-12}$-groups are present;
said synthetic polypeptide having at least about 10% of the antigenicity of that of biologic heat stable enterotoxin of *Escherichia coli* and having thin layer chromatographic and electrophoretic mobilities different from said biologic heat stable enterotoxin.

6. A synthetic polypeptide, taken from left to right in the direction from amino-terminus to carboxy-terminus, represented by the formula:

$$R_a{}^1$$
Asn(Ser)Thr(Ser)Phe(Asn)TyrCys($R_g{}^7$)

-continued

CysGluLeuCysCysTyr(Asn)ProAlaCys($R_k{}^{11}$)Ala(Thr)
  |
  $R_c{}^5$
GlyCysAsn(Tyr)

wherein lines connecting two Cys residues represent disulfide bonds of cystine residues;
$R_a{}^1$ and $R_c{}^5$ are the same or different moieties bonded to the sulfur atom of the Cys residue. "a" and "e" are integers having a value of zero or one, with the proviso that "e" is zero when "a" is zero, and the further proviso that when "a" is zero an intramolecular disulfide bond is present between the Cys residues shown in said formula as bonded to said $R_a{}^1$ and $R_c{}^5$, and when the value of "a" and "e" are one said $R_a{}^1$ and $R_c{}^5$ are selected from the group consisting of hydrogen carboxamidomethyl and carboxymethyl;
$R_i{}^9$ and $R_k{}^{11}$ are alternative Ser amino acid residues to the preceding Cys residue shown in the formula, wherein "i" and "k" are integers having the value of zero or one with the proviso that when "a" is zero, "i" and "k" are zero, and when "a" is one said $R_i{}^9$ and $R_k{}^{11}$ are present; and
said polypeptide having at least about 10% of the antigenicity of that of biologic heat stable enterotoxin of *Escherichia coli* and having thin layer chromatographic and electrophoretic mobilities different from said biologic heat stable enterotoxin.

7. A synthetic polypeptide, taken from left to right and in the direction from amino-terminus to carboxy-terminus, represented by the formula:

$R_a{}^1$  $R_b{}^2$
|  |
Asn(Ser)Thr(Ser)Phe(Asn)TyrCys($R_g{}^7$)Cys($R_h{}^8$)Glu $R_c{}^3$  $R_d{}^4$  $R_e{}^5$
|  |  |
LeuCyS($R_i{}^9$)Cys($R_j{}^{10}$)Tyr(Asn)ProAlaCys($R_k{}^{11}$)Ala(Thr)

$R_f{}^6$
|
GlyCys($R_l{}^{12}$)Asn(Tyr)

wherein a-f and g-l are integers each having a value of zero or one, whereby if the value of any of a-f or g-l is zero, the corresponding $R_{a-f}{}^{1-6}$- or $R_{g-l}{}^{7-12}$-group is absent, while if the value of any of a-f or g-l is one, the corresponding $R_{a-f}{}^{1-6}$- or $R_{g-l}{}^{7-12}$-group is present;
the $R_{a-f}{}^{1-6}$-groups when taken individually are the same or different moieties bonded to the sulfur atom of the respective Cys residues of said formula, and are selected from the group consisting of hydrogen, carboxamidomethyl and carboxymethyl;
the $R_{g-l}{}^{7-12}$-groups are alternative Ser residues to the immediately preceding Cys residues shown in said formula; and
at least two of said a-f and two of said g-l are zero, to provide at least one pair of non-contiguous Cys residues whose $R_{a-f}{}^{1-6}$-groups are absent, with the proviso that said synthetic polypeptide contains at least one intramolecular cystine disulfide bond formed from said at least two non-contiguous Cys residues;
said polypeptide having at least about 10% of the antigenicity of that of biologic heat-stable enterotoxin of *Escherichia coli* and having thin layer chromatographic and electrophoretic mobilities different from said biologic heat stable enterotoxin.

8. The synthetic polypeptide according to claim 7 wherein the values of g-1 are one for only one pair of residues of the pairs of $R_g$-$l^{7-12}$ Ser residues selected from the group consisting of $R_g^7$ and $R_k^{11}$, $R_h^8$ and $R_j^{10}$, $R_i^9$ and $R_l^{12}$, $R_h^8$ and $R_i^9$, and $R_k^{11}$.

9. The synthetic polypeptide according to claim 1 wherein the values of said g-1 are one for only one pair of residues of the pairs of $R_g$-$l^{7-12}$ residues selected from the group consisting of $R_g^7$ and $R_k^{11}$, $R_i^9$ and $R_l^{12}$, $R_h^8$ and $R_j^{10}$.

10. A synthetic polypeptide having at least about 10% of the antigenicity of that of biological heat stable enterotoxin of *Escherichia coli* and having thin layer and electrophoretic mobilities different from said biologic heat stable enterotoxin, said polypeptide having the amino acid residue sequence, taken from left to right and in the direction from amino-terminus to carboxyterminus, represented by the formula:

```
    ┌─────────────────────────┐
AsnThrPheTyrCysCysGluLeuCysCys
          └──┐    └──┐
TyrProAlaCysAlaGlyCysAsn
``` wherein the lines connecting the Cys residues represent disulfide bonds between those residues.

11. The synthetic polypeptide according to claim 1 containing at least two cystine residues formed between the pairs of Cys residues shown in said formula as bonded to groups $R_a^1$ and $R_e^5$, $R_b^2$ and $R_d^4$, or $R_c^3$ and $R_f^6$.

12. The synthetic polypeptide according to claim 1 containing three cystine residues formed between the pairs of Cys residues shown in said formula as bonded to groups $R_a^1$ and $R_e^5$, $R_b^2$ and $R_d^4$, and $R_c^3$ and $R_f^6$.

* * * * *

UNITED STATES PATENT AND TRADEMARK OFFICE
CERTIFICATE OF CORRECTION

PATENT NO. : 4,545,931

DATED : October 8, 1985

INVENTOR(S) : Richard A. Houghten

It is certified that error appears in the above-identified patent and that said Letters Patent is hereby corrected as shown below:

Throughout patent, all occurrences, where designations are printed in the format "$R_x\ y$", where x represents an alphabetical designation and y represents a numerical designation, change to --$R_x^y$--, for example, at Column 4, line 37, "$R_f\ 6$" should be --$R_f^6$-- and at Column 4, line 28, "$R_{g-1}\ 7\text{-}12$" should be --$R_{g-1}^{7-12}$--

Column 5, line 11, delete subscript "g-1" and insert lowercase --g-1--

Column 5, line 14, after "residues" insert --being selected from the group consisting of the Cys residues--

Column 18, lines 19-20, delete "$(R_1\ 1\text{-}2)$ and insert --$(R_1^{12})$--

Column 18, lines 41-42, delete "g-11" and insert --g-1--
42, delete "g-1" and insert --g-1--

UNITED STATES PATENT AND TRADEMARK OFFICE
CERTIFICATE OF CORRECTION

PATENT NO. : 4,545,931

DATED : October 8, 1985

INVENTOR(S) : Richard A. Houghten

It is certified that error appears in the above-identified patent and that said Letters Patent is hereby corrected as shown below:

Column 22, line 8, after "synthetic", insert --ST prepared--

Signed and Sealed this

Twenty-third Day of August, 1988

*Attest:*

DONALD J. QUIGG

*Attesting Officer*   *Commissioner of Patents and Trademarks*